US005723292A

United States Patent [19]
Kawasaki et al.

[11] Patent Number: 5,723,292
[45] Date of Patent: *Mar. 3, 1998

[54] STABLE DNA CONSTRUCTS

[75] Inventors: Glenn H. Kawasaki, Seattle, Wash.; Leslie Bell, Princeton, N.J.; Meher Irani, Seattle, Wash.

[73] Assignee: ZymoGenetics, Inc., Seattle, Wash.

[*] Notice: The term of this patent shall not extend beyond the expiration date of Pat. No. 5,527,668.

[21] Appl. No.: 488,179

[22] Filed: Jun. 7, 1995

Related U.S. Application Data

[63] Continuation of Ser. No. 293,568, Aug. 22, 1994, which is a continuation of Ser. No. 136,472, Oct. 12, 1993, abandoned, which is a continuation of Ser. No. 587,613, Sep. 20, 1990, abandoned, which is a continuation-in-part of Ser. No. 734,119, May 15, 1985, abandoned, which is a continuation-in-part of Ser. No. 614,734, May 25, 1984, abandoned.

[51] Int. Cl.$^6$ ..................................................... C12P 21/02
[52] U.S. Cl. .................. 435/6; 435/69.1; 435/71.1; 435/171; 435/172.3; 435/254.2; 435/254.21; 435/255.21
[58] Field of Search ............... 435/171, 6, 171.1, 435/69.1, 254.2, 254.21, 320.1, 172.3, 71.1, 255.21; 536/232, 23.74

[56] References Cited

U.S. PATENT DOCUMENTS

| | | | |
|---|---|---|---|
| 4,237,244 | 12/1980 | Cohen et al. | 525/171 |
| 4,371,615 | 2/1983 | Miwa et al. | 435/172.3 |
| 4,506,013 | 3/1985 | Hershberger et al. | 435/34 |
| 4,599,311 | 7/1986 | Kawasaki | 435/69.2 |
| 4,931,373 | 6/1990 | Kawasaki et al. | 435/69.2 |
| 5,527,668 | 6/1996 | Kawasaki et al. | 435/6 |

FOREIGN PATENT DOCUMENTS

| | | | |
|---|---|---|---|
| 0 100 561 A1 | 2/1984 | European Pat. Off. | C12N 15/00 |
| 0 184 438 A2 | 6/1986 | European Pat. Off. | C12N 15/00 |
| WO 86/03774 | 7/1986 | WIPO | C12N 15/00 |

OTHER PUBLICATIONS

Nagley, P. et al. 1983 in. Manipulation and Expression of Genes in Furkayotes. Academic Press, New York. pp. 293–302.

N. Pagratis pp. 5–9 and Pavlakis et al. pp. 29–38 in Current Communications in Mol. Biology. Miker et al (eds). 1987.

Carrell et al., "Structure and Variation of Human $\alpha_1$–Antitrypsin." *Nature* 298:239–334, 1982.

Owen et al., "Mutation of Antitrypsin to Antithrombin." *New Eng. J. Med.* 309:694–698, 1983.

Cohen et al., "Functional expression in yeast of the *Escherichia coli* plasmid gene coding for chloramphenicol acetyltransferase." *PNAS* 77:1078–1082, 1980.

Dickson. "Expression of a foreign eukaryotic gene in *Saccharomyces cerevisiae*: β–galactosidase from *Kluyveromyces lactis*," *Gene* 10:347–356, 1980.

Carbon et al., "The Expression of Yeast DNA in *Escherichia coli*," *Ninth Miami Winter Symposia* 13/14:59–72, 1977.

Carbon and Ratzkin, "The Expression of Eukaryotic DNA Segments in *Escherichia coli*", *J. Supramolec. Struct.* Suppl. 1, 46, 1977.

Struhl et al., "Functional genetic expression of eukaryotic DNA in *Escherichia coli*," *PNAS* 73:1471–1475, 1976.

Beach et al., "Functionally homologous cell cycle control genes in budding and fission yeast," *Nature* 300:706–709, 1982.

Jasin and Schimmel, "Delection of an Essential Gene in *Escherichia coli* by Site–Specific Recombination with Linear DNA Fragments." *J. Bact.* 159:783–786, 1984.

Maniatis, T. et al., *Molecular Cloning,: A laboratory manual*, Cold Springs Harbor Laboratory, 1982, p. 57.

Hopwood, D.A. et al., *Genetic manipulation of Streptomyces: A Laboratory Manual*, The John Innes Foundation, Norwich, 1985, pp. 112–113.

Rodriguez, R.L. and R.C. Tait, *Recombinant DNA Techniques: An Introduction*, Addison–Wesley Publishing Company, Canada, 1983, pp. 27–29.

Kuo and Campbell, "Cloning of *Saccharomyces cerevisiae*–DNA Replication Genes Isolation of the CDC8Gene and Two Genes That Compensate for the cdc8–1 Mutation." *Mol. Cell. Biol.* 3:1730–1737, 1983.

Carter et al., "Genetic Control of Cell Proliferation" *Yeast Genetics*, Spencer et al. (Editors) Springer–Verlag, NY pp. 1–28, 1983.

Alber and Kawasaki, "Nucleotide Sequence of the Triose Phosphate Isomerase Gene of *Saccharomyces cerevisiae*," *J. Mol. Appl. Gen.* 1:419–434, 1982.

Nasmyth and Reed, "Isolation of genes by complementation in yeast: Molecular cloning of a cell–cycle gene," *Proc. Natl. Acad. Sci. USA* 77(4)2119–2123, 1980.

Arendes et al., "Yeast 2-μm plasmid DNA replication in vitro: Purification of the CDC8 gen product by complementation assay," *Proc. Natl. Acad. Sci. USA* 80:673–677, 1983.

Walsh et al., "Cloning of Genes That Complement Yeast Hexokinase and Glucokinase Mutants," *J. Bact.* 154:1002–1004, 1983.

Nurse and Bissett, "Gene required in $G_1$ for commitment to cell cycle and in $G_2$ for control o mitosis in fission yeast." *Nature* 292:558–560, 1981.

(List continued on next page.)

Primary Examiner—James Ketter
Assistant Examiner—Iram Yucel
Attorney, Agent, or Firm—Gary E. Parker

[57] ABSTRACT

Methods are provided for producing protein products in host cells and for selecting transformed cells comprising the step of transforming the host cell with a DNA molecule comprising a gene which complements a deficiency in the host cell. The host cell is s strain having a deficiency in a function necessary for normal cell growth. The gene in the DNA molecule, such as a plasmid, which complements the deficiency serves as a selection marker whereby the growth conditions for selection may comprise a conventional complex medium.

20 Claims, 21 Drawing Sheets

OTHER PUBLICATIONS

Suggs et al., "Use of synthetic oligonucleotides as hybridization probes: Isolation of cloned cDNA sequences for human $\beta_2$-microglobulin," *PNAS USA* 78(11):6613–6617, 1981.

Bollen et al., "Cloning and Expression in *Escherichia coli* of Full–Length Complementary DNA Coding for Human $\alpha$–Antitrypsin," *DNA* 2:255–264, 1983.

Das and Hollenberg, "A High–Frequency Transformation System for the Yeast *Kluyveromyces lactis*," *Current Genetics* 6:123–128, 1982.

Berse et al., "Cloning and characterization of the ornithine carbamoyltransferase gene from *Aspergillus nidulans*," *Gene* 25:109–117, 1983.

Russell, "Evolutionary divergence of the mRNA transcription initiation mechanism in yeast," *Nature* 301:167–169, 1983.

Russel, "Transcription of the triose–phosphate–isomerase gene of *Schizosaccharomyces pombe* initiates from a start point different from that in *Saccharomyces cerevisiae*," *Gene* 40:125–130, 1985.

Rothstein, "One–Step Gene Disruption in Yeast," *Meth. in Enz.* 101:202–211, 1983.

Clarke and Carbon, "Functional Expression of Cloned Yeast DNA in *Escherichia coli*: Specific Complementation of Argininosuccinate Lyase (argH) Mutations," *J. Mol. Biol.* 120:517–532, 1978.

Ilgen et al., "Transformation of Yeast," *Genetic Engineering: Principles and Methods* 1:117–132, 1979.

Hsiao and Carbon, "High–frequency transformation of yeast by plasmids containing the cloned yeat ARG4 gene," *PNAS USA* 76(8):3829–3833, 1979.

Carbon et al., "The Isolation and Charcterization of Specific Gene Sysstems from the Yeast, *Saccharomyces cerevisiae*," *Biochem. and Gene. of Yeasts* 425–443, 1978.

Banks, "Transformation of *Ustilago maydis* by a Plasmid Containing Yeast 2–Micron DNA," *Current Genetics* 7:73–77, 1983.

Williamson et al., "Isolation of the structural gene for alcohol dehydrogenase by genetic complementation in yeast," *Nature* 283:214–216, 1980.

Henikoff et al., "Isolation of a gene from Drosophila by complementation in yeast," *Nature* 289:33–37, 1981.

Bennetzen, "An Analysis of Gene Structure and Expression in the Yeast *Saccharomyces cerevisiae*," *Doctoral dissertation*, p. 118, University of Washington, 1980.

Hartwell et al., "Genetic Control of the Cell Division Cycle in Yeast: V. Genetic Analysis of cdc Mutants," *Genetics* 74:267–286, 1973.

Gleeson et al., "Transformation of the Methylotrophic Yeast *Hansenula polymorpha*," *J. of Gen. Micro.* 132:3459–3465, 1986.

Stinchcomb et al., "Centromeric DNA from *Saccharomyces cerevisiae*," *J. Mol. Biol.* 158:157–179, 1982.

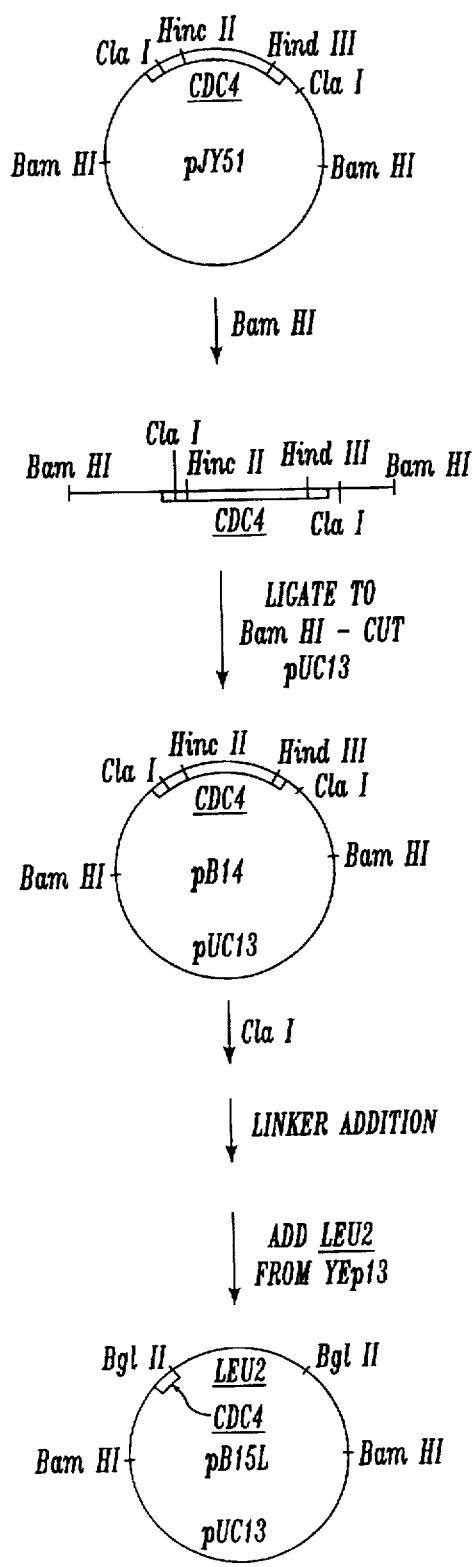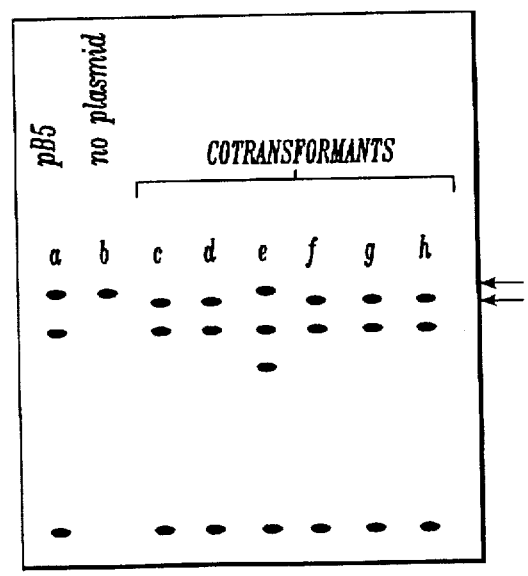
Fig. 3.
Fig. 4.

SEQUENCE COMPARISON OF S. POMBE AND S. CEREVISIAE GENES FOR TRIOSE PHOSPHATE ISOMERASE (POT1 AND TPI1)

```
                    -150       -140       -130       -120       -110       -100
S. pombe            GGATCCATGCCAACGGTTGCTATCGACGGGGTAAATTGCCCGAAGCTCGGTAATTCCCCT
S. cerevisiae       AATTTAGGAGTTTAGTGAACTTGCAACATTTACTATTTTCCCTTCTTACGTAAATATTT -90        -80        -70        -60        -50        -40
S. pombe            TAACTGTGTGACTGTCCGCTACGTTATATATAATGAGCGGACGGGCCAACTCTCGTCTC
S. cerevisiae       TTCTTTTTAATTCTAAATCAATCTTTTTCAATTTTTTGTTTGTATTCTTTTCTTGCTTA -30        -20        -10       -1  1            10
S. pombe            TCCCCAACTACATTTCAATAGTAGAACTAGGATCAAA ATG GCA CGT AAA TTC
S. cerevisiae       AATCTATAACTACAAAAAACACATACATAAACTAAAA ATG GCT AGA ACT TTC S. pombe                                                  MET ALA ARG LYS PHE
S. cerevisiae                                             (Met)        Thr 20         30         40         50         60
S. pombe            TTT GTC GGT GGT AAC TTT AAG ATG AAT GGC TCT TTG GAG TCC ATG
S. cerevisiae       TTT GTC GGT GGT AAC TTT AAA TTA AAC GGT TCC AAA CAA TCC ATT S. pombe            PHE VAL GLY GLY ASN PHE LYS MET ASN GLY SER LEU GLU SER MET
S. cerevisiae                               Leu     Lys     Gln         Ile 70         80         90        100
S. pombe            AAG ACT ATT ATT GAG GGT TTG AAC ACC ACC AAG CTT AAC GTT GGT
S. cerevisiae       AAG GAA ATT GTT GAA AGA TTG AAC ACT GCT TCT ATC CCA GAA AAT S. pombe            LYS THR ILE ILE GLU GLY LEU ASN THR THR LYS LEU ASN VAL GLY
S. cerevisiae           Glu     Val     Arg                 Ala Ser Ile Pro Glu Asn 110        120        130        140        150
S. pombe            GAT GTC GAA ACT GTC ATC TTC CCT CAA AAC ATG TAC CTC ATC ACC
S. cerevisiae       GTC GAA GTT GTT ATC TGT CCT CCA GCT ACC TAC TTA GAC TAC TCT S. pombe            ASP VAL GLU THR VAL ILE PHE PRO GLN ASN MET TYR LEU ILE THR
S. cerevisiae       Val Glu Val Val Ile Cys Pro     Ala Thr Tyr Leu Asp Tyr Ser
```

FIG.—5A

|  | | 160 | | 170 | | 180 | | 190 | |
|---|---|---|---|---|---|---|---|---|---|
| S. pombe | ACC | CGC | CAA | CAA | GTC | AAG | AAG | GAT | ATT | GGC | GTT | GGT | GCC | CAA | AAC |
| S. cerevisiae | GTC | TCT | TTG | GTT | AAG | AAG | CCA | CAA | GTC | ACT | GTC | GGT | GCT | CAA | AAC |

| S. pombe | THR | ARG | GLN | GLN | VAL | LYS | LYS | ASP | ILE | GLY | VAL | GLY | ALA | GLN | ASN |
| S. cerevisiae | Val | Ser | Leu | Val | Lys | | Pro | Gln | Val | Thr | | | | | |

|  | | 200 | | 210 | | 220 | | 230 | | 240 |
|---|---|---|---|---|---|---|---|---|---|---|
| S. pombe | GTC | TTC | GAC | AAG | AAG | AAC | GGT | GCC | TAC | ACT | GGT | GAG | AAC | AGT | GCT |
| S. cerevisiae | GCC | TAC | TTG | AAG | GCT | TCT | GGT | GCT | TTC | ACC | GGT | GAA | AAC | TCC | GTT |

| S. pombe | VAL | PHE | ASP | LYS | LYS | ASN | GLY | ALA | TYR | THR | GLY | GLU | ASN | SER | ALA |
| S. cerevisiae | Ala | Tyr | Leu | | Ala | Ser | | | Phe | | | | | | Val |

|  | | 250 | | 260 | | 270 | | 280 | |
|---|---|---|---|---|---|---|---|---|---|
| S. pombe | CAA | TCT | TTG | ATT | GAT | GCT | GGT | ATT | ACC | TAC | ACT | TTG | ACT | GGT | CAC |
| S. cerevisiae | GAC | CAA | ATC | AAG | GAT | GTT | GGT | GCT | AAG | TGG | GTT | ATT | TTG | GGT | CAC |

| S. pombe | GLN | SER | LEU | ILE | ASP | ALA | GLY | ILE | THR | TYR | THR | LEU | THR | GLY | HIS |
| S. cerevisiae | Asp | Gln | Ile | Lys | | Val | | Ala | Lys | Trp | Val | Ile | Leu | | |

|  | | 290 | | 300 | | 310 | | 320 | | 330 |
|---|---|---|---|---|---|---|---|---|---|---|
| S. pombe | TCC | GAG | CGT | CGT | ACC | ATC | TTC | AAG | GAG | TCT | GAC | GAG | TTC | GTT | GCC |
| S. cerevisiae | TCC | GAA | AGA | AGA | TCT | TAC | TTC | CAC | GAA | GAT | GAC | AAG | TTC | ATT | GCT |

| S. pombe | SER | GLU | ARG | ARG | THR | ILE | PHE | LYS | GLU | SER | ASP | GLU | PHE | VAL | ALA |
| S. cerevisiae | | | Ser | Tyr | | | His | | Asp | | | Lys | | Ile | |

|  | | 340 | | 350 | | 360 | | 370 | |
|---|---|---|---|---|---|---|---|---|---|
| S. pombe | GAC | AAG | ACC | AAG | TTT | GCC | CTT | GAA | CAA | GGT | CTT | ACT | GTC | GTT | GCC |
| S. cerevisiae | GAC | AAG | ACC | AAG | TTC | GCT | TTA | GGT | CAA | GGT | GTC | GGT | GTC | ATC | TGT |

| S. pombe | ASP | LYS | THR | LYS | PHE | ALA | LEU | GLU | GLN | GLY | LEU | THR | VAL | VAL | ALA |
| S. cerevisiae | | | | | | | | Gly | | | Val | Gly | | Ile | Leu |

|  | | 380 | | 390 | | 400 | | 410 | | 420 |
|---|---|---|---|---|---|---|---|---|---|---|
| S. pombe | TGC | ATT | GGT | GAG | ACT | TTG | GCC | GAC | CGT | GAG | GCT | AAC | GAG | ACC | ATC |
| S. cerevisiae | TGT | ATC | GGT | GAA | ACT | TTG | GAA | GAA | AAG | AAG | GCC | GGT | AAG | ACT | TTG |

| S. pombe | CYS | ILE | GLY | GLU | THR | LEU | ALA | ASP | ARG | GLU | ALA | ASN | GLU | THR | ILE |
| S. cerevisiae | | | | | | | | Glu | Glu | Lys | Lys | | Gly | Lys | Leu |

FIG.—5B

|              |                                                         |
|--------------|---------------------------------------------------------|
|              | 430     440     450     460 |
| S. pombe     | ACC GTT GTT GTT CGT CAA TTG AAC GCC ATC GCT GAC AAG CTC CAG |
| S. cerevisiae| GAT GTT GTT GAA AGA CAA TTG AAC GCT GTC TTG GAA GAA GTT AAG |
| S. pombe     | THR VAL VAL VAL ARG GLN LEU ASN ALA ILE ALA ASP LYS VAL GLN |
| S. cerevisiae| Asp     Glu                        Val Leu Glu Glu     Lys |

470     480     490     500     510

S. pombe      AAC TGG TCC AAG ATT GTC ATT GCT TAT GAG CCT GTC TGG GCC ATT
S. cerevisiae  GAC TGG ACT AAC GTC GTT GTC GCT TAC GAA CCA GTC TGG GCC ATT S. pombe      ASN TRP SER LYS ILE VAL ILE ALA TYR GLU PRO VAL TRP ALA ILE
S. cerevisiae  Asp      Thr Asn Val      Val 520     530     540     550

S. pombe      GGT ACT GGT AAG ACT GGC ACC CCT GAG GAA GCT CAA GAG GTT CAC
S. cerevisiae  GGT ACC GGT TTG GCT GCT ACT CCA GAA GAT GCT CAA GAT ATT CAC S. pombe      GLY THR GLY LYS THR GLY THR PRO GLU GLU ALA GLN GLU VAL HIS
S. cerevisiae                   Leu Ala Ala          Asp      Asp Ile 560     570     580     590     600

S. pombe      GCT GAG ATC CGC AAG TGG GCT ACC AAC AAG CTT GGT GCA TCT GTT
S. cerevisiae  GCT TCC ATC AGA AAG TTC TTG GCT TCC AAG TTG GGT GAC AAG GCT S. pombe      ALA GLU ILE ARG LYS TRP ALA THR ASN LYS LEU GLY ALA SER VAL
S. cerevisiae      Ser           Phe Leu Ala Ser          Asp Lys Ala 610     620     630     640

S. pombe      GCC GAG GGT CTC CGT GTC ATC TAC GGT GGT TCC GTT ACC GGT GGT
S. cerevisiae  GCC AGC GAA TTG AGA ATC TTA TAC GGT GGT TCC GCT AAC GGT AGC S. pombe      ALA GLU GLY LEU ARG VAL ILE TYR GLY GLY SER VAL THR GLY GLY
S. cerevisiae      Ser Glu      Ile Leu               Ala Asn      Ser 650     660     670     680     690

S. pombe      AAC TGC AAG GAG TTC CTC AAG TTC CAC GAT ATT GAC GGT TTC TTG
S. cerevisiae  AAC GCC GTT ACC TTC AAG GAC AAG GCT GAT GTC GAT GGT TTC TTG S. pombe      ASN CYS LYS GLU PHE LEU LYS PHE HIS ASP ILE ASP GLY PHE LEU
S. cerevisiae      Ala Val Thr      Lys Asp Lys Ala      Val

FIG.—5C

```
                    700         710         720         730
S. pombe        GTT GGC GGT GCT TCT CTC AAG CCT GAA TTC CCT ACT AAC ATT CTT
S. cerevisiae   GTC GGT GGT GCT TCT TTG AAG CCA GAA TTT GTT GAT ATC ATC AAC S. pombe        VAL GLY GLY ALA SER LEU LYS PRO GLU PHE PRO THR ASN ILE VAL
S. cerevisiae                                           Val Asp Ile     Asn 740         750  +1        +10       +20       +30
S. pombe        AAT GTT CAC AGC CTT TAA AAACGTGCATAGACGTTTTATTTGGCGTAAAGCGA
S. cerevisiae   TCT AGA AAC TAA         GATTAATATAATTATATAAAAATATTATCTTCTTT S. pombe        ASN VAL HIS SER LEU ***
S. cerevisiae   Ser Arg Asn ***

+40       +50       +60       +70       +80       +90
S. pombe        ATGACTTTTTTATTCCTTTAGCTTTTTGTCTTTAATGAATAGGGATTTTTTTATATCCT
S. cerevisiae   TCTTTATATCTAGTGTTATGTAAAATAAATTGATGACTACGGAAAGCTTTTTTATATTG +100      +110      +120      +130
S. pombe        AATTTTTTTACAAGCAATATTTGATTTATTTTTATTTGCT
S. cerevisiae   TTTCTTTTTCATTCTGAGCCACTTAAATTTCGTGAATGT
```

FIG.—5D

G AATTCATCGATATCTAGATCTCGAGCTCGCGAA AGCTT
Eco RI   Eco RV Bgl II  Sac I      Hind III
     Cla I   Xba I  Xho I  Nru I

Fig. 9.

STABLE DNA CONSTRUCTS

CROSS-REFERENCE TO RELATED APPLICATION

This application is a continuation of U.S. patent application Ser. No. 08/293,568, filed Aug. 22, 1994, which was a continuation of U.S. patent application Ser. No. 08/136,472, filed Oct. 12, 1993, now abandoned, which was a continuation of U.S. patent application Ser. No. 07/587,613, filed Sep. 20, 1990, now abandoned, which was a continuation of U.S. patent application Ser. No. 07/001,710, filed Jan. 9, 1987, now abandoned, which was a continuation-in-part of U.S. patent application Ser. No. 06/734,119, filed May 15, 1985, abandoned, which was a continuation-in-part of U.S. patent application Ser. No. 06/614,734, filed May 25, 1984, now abandoned.

BACKGROUND OF THE INVENTION

The use of microorganisms for the production of useful polypeptide products through recombinant DNA technology is becoming established as an industry. Foreign genetic material may be introduced into a culture of microorganisms, and, given the proper intracellular and extracellular conditions, the desired protein product(s) may be synthesized from the foreign gene(s). Such genetic material is commonly introduced into microorganisms in the form of plasmids, which are autonomously replicating extra-chromosomal elements. In order to ensure the maintenance of plasmids within a culture of transformed cells, it has been necessary to grow those cells under special conditions. In the absence of such conditions, the plasmids, which may be inherently unstable, will not be maintained, and the cell population will revert to the untransformed state.

Increased plasmid stability and copy number are important to the biotechnology industry as a means of maintaining the production of plasmid-encoded proteins at a consistently high level. Previously reported attempts to increase plasmid stability do not appear to be optimal for commercial application. The introduction of yeast centromeres into ARS-bearing plasmids, while enhancing stability, has been shown to markedly decrease plasmid copy number (Clarke and Carbon, *Nature* 287:504–509, 1980 and Stinchcomb, .et al., *J. Molec. Biol.* 158:157–179, 1982). Linear centromeric yeast plasmids similarly show an inverse relationship between stability and copy number (Murray and Szostak, *Nature* 305:189–193, 1983).

Plasmids typically contain gene sequences, known as selectable markers, which encode antibiotic resistance or complement nutritional requirements of the host cell. To select for the presence of such plasmids, transformed cells must thus be grown in special media which contain a selective drug or which are depleted for specific nutrients. These media requirements may be both expensive and prohibitive of optimal cell growth rates during the large-scale fermentation process. Many of such plasmids have been reported in the literature. Those comprising antibiotic drug resistance genes include pBR322 (Bolivar, et al., *Gene* 2:95–113, 1977) and its derivatives, such as the pUC vectors (Vieira and Messing, *Gene* 19:259–268, 1982) which carry a gene for ampicillin resistance; and pBR325 (Prentki, et al., *Gene* 14:289, 1981) which carries resistance genes for ampicillin, tetracycline, and chloramphenicol. Plasmids which complement host nutrient requirements include the yeast vectors YEp13 (Broach, et al., *Gene* 8:121–133, 1979), which carries the LEU2 gene; and YRp7' (Stinchcomb, et al., *Nature* 282:39, 1979), which carries the TRP1 gene.

Mammalian cell selection systems include the use of the dihydrofolate reductase (DHFR) gene which confers resistance to methotrexate (reviewed by Schimke, *Cell* 37:705–713, 1984) and antibiotic resistance, such as resistance to G418 (Southern and Berg, *J. Mol. Appl. Genet.* 1:327–341, 1982).

It is therefore an object of the present invention to provide DNA constructs containing, as selectable markers, gene sequences whose products are essential for the viability or normal growth of the host cell on complex media.

It is another object of the present invention to provide recombinant host cells containing DNA constructs which are selectable by growth on complex media.

It is a further object of the present invention to provide cells deficient in essential functions which may act as hosts for DNA constructs carrying gene sequences which complement these defective essential functions.

It is yet another object of the present invention to provide methods for producing foreign proteins in recombinant host cells, wherein the proteins are the products of genes carried on DNA constructs which contain, as selectable markers, gene sequences which complement a deficiency in an essential gene in the host cells.

Other objects of the invention will become apparent to those skilled in the art.

SUMMARY OF THE INVENTION

According to the present invention, there are provided DNA constructs and appropriate host cells such that the constructs are maintained at high copy number without the need for special selective media. Growth in such conditions may result in faster cell division, greater cell density, and reduced production costs.

The present invention further provides a method for producing protein products in a host cell having a deficiency in a function necessary for normal cell growth in complex media, comprising the step of transforming the host cell with a DNA construct comprising a gene which complements the deficiency and a sequence coding for the protein product(s). The present method also provides DNA constructs, particularly plasmids, and transformant strains containing these constructs.

As used herein the term "DNA construct" means any DNA molecule which has been modified by man in a manner such that the nucleotide sequences in the molecule are not identical to a sequence which is produced naturally. The term "DNA construct" also includes clones of DNA molecules which have been so modified. The term "expression vector" is defined as a DNA construct which includes sequences which provide for its replication in a host cell, either autonomously or through integration into the host cell genome, a site of transcription initiation and at least one structural gene coding for a protein which is to be expressed in the host cell. The expression vector will usually also contain appropriate control regions such as a promoter and terminator which control the expression of the protein in the host organism. Expression vectors according to the present invention will also contain a selectable marker comprising an essential gene as described herein.

The term "plasmid" will have its commonly accepted meaning, i.e., autonomously replicating, usually close-looped, DNA.

The term "gene" will include both genomic DNA sequences and corresponding cDNA sequences.

In the accompanying drawings:

FIG. 3 illustrates the construction of plasmid pB15L.

FIG. 4 shows a Southern blot of DNA from *S. cerevisiae* strain A2.7.c co-transformed with plasmids pB5 and pB15L. The blot was probed with a 2.5 kb BamHI-HindIII fragment from the 5' flanking region of CDC4 in order to test for disruption of the genomic CDC4 locus. Lane a contains DNA from cells transformed with pB5 alone; Lane b, untransformed cells; Lanes c-h, co-transformants. Arrows indicate the genomic fragments hybridizing to the probe.

FIGS. 5A-5D shows the sequences of the *S. pombe* POT1 and *S. cerevisiae* TPI1 genes together with the respective inferred protein sequences. The entire *S. pombe* TPI protein sequence inferred from the DNA sequence of the POT1 gene is given. The sequence of the *S. cerevisiae* protein is given only where it differs from the *S. pombe* sequence. The methionine at position 1 in the *S. cerevisiae* protein sequence inferred from the DNA sequence of TPI1 is not present in the mature protein.

Figure 6:
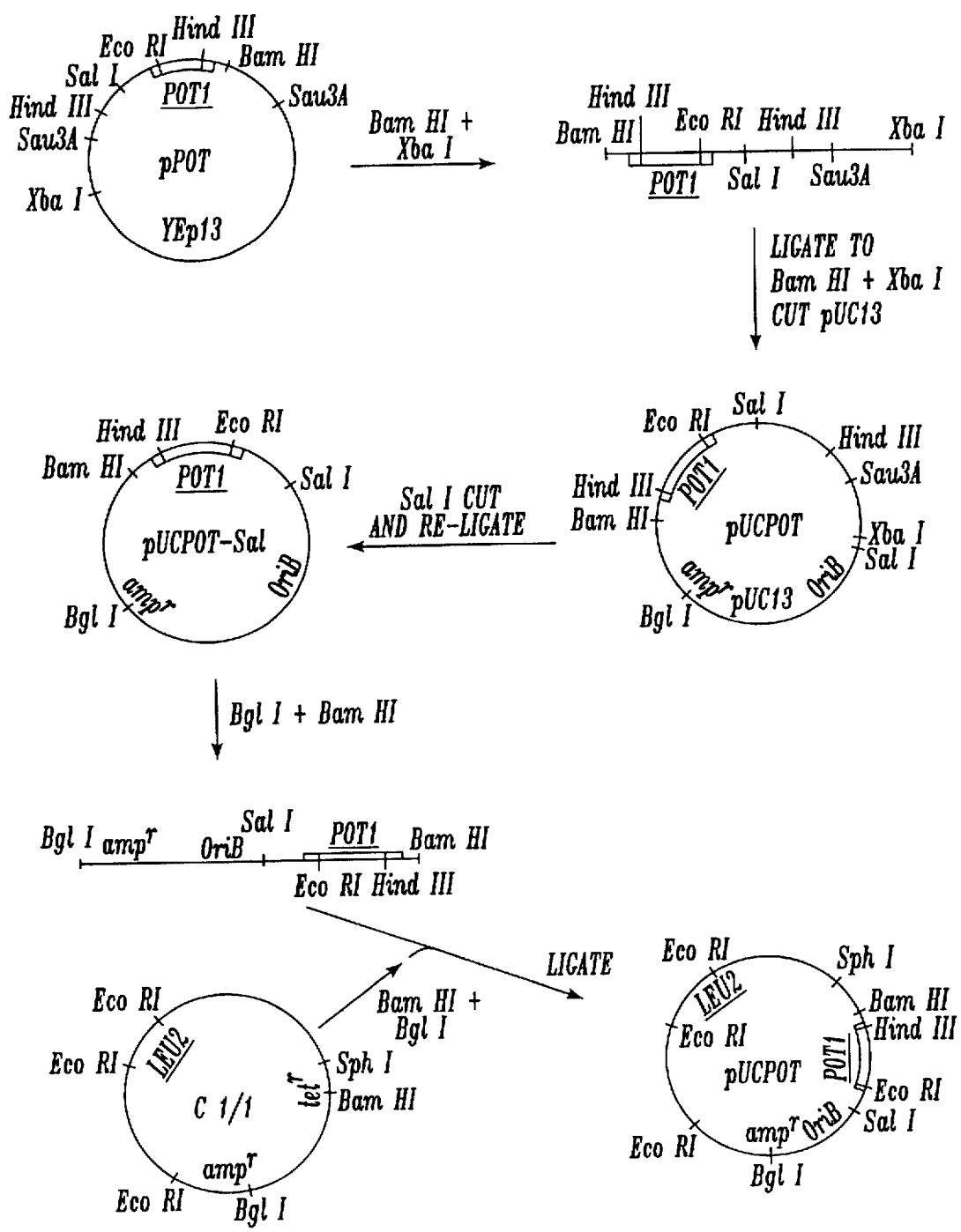

FIG. 6 illustrates the construction of the plasmid pCPOT.

Figure 7:
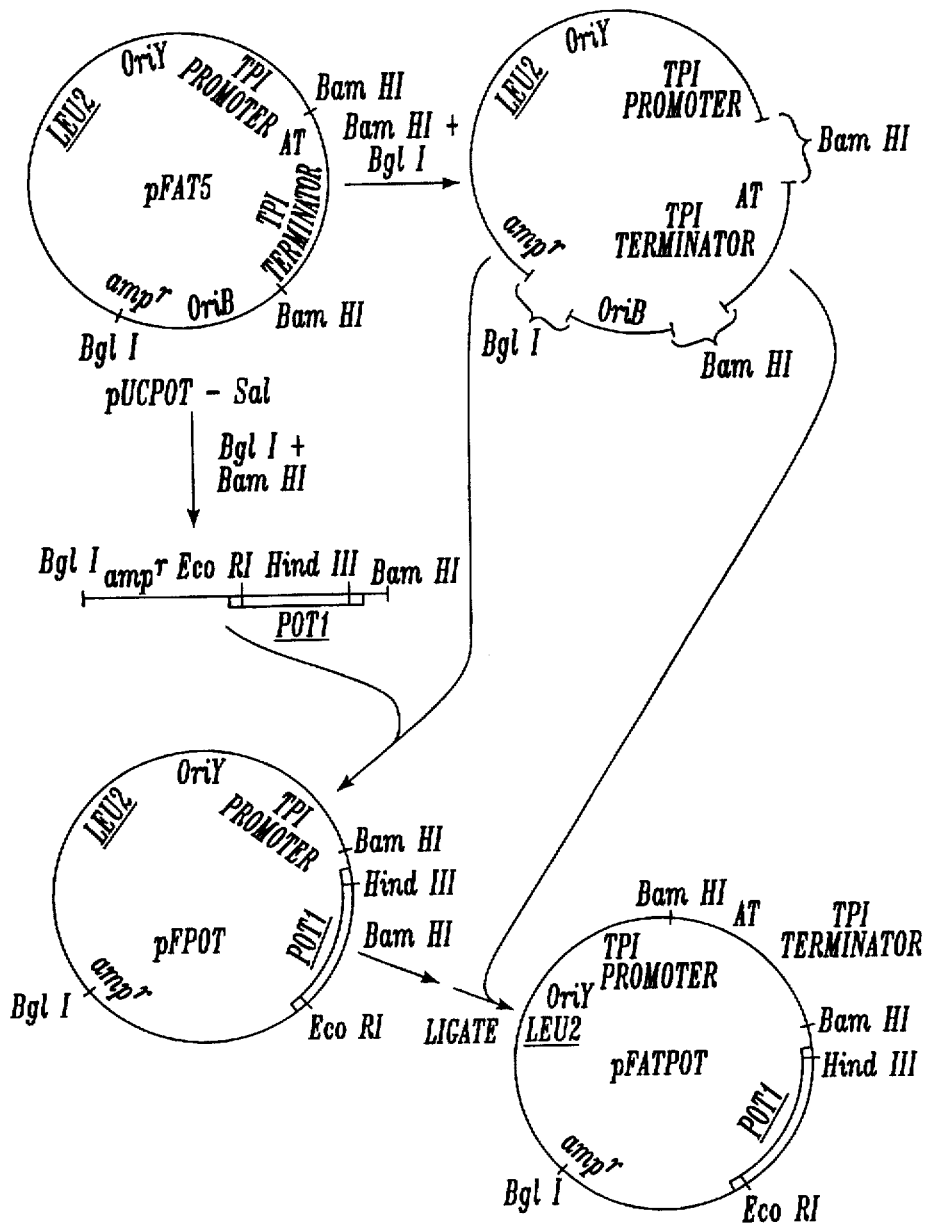

FIG. 7 illustrates the construction of the plasmid pFAT-POT.

Figure 8:
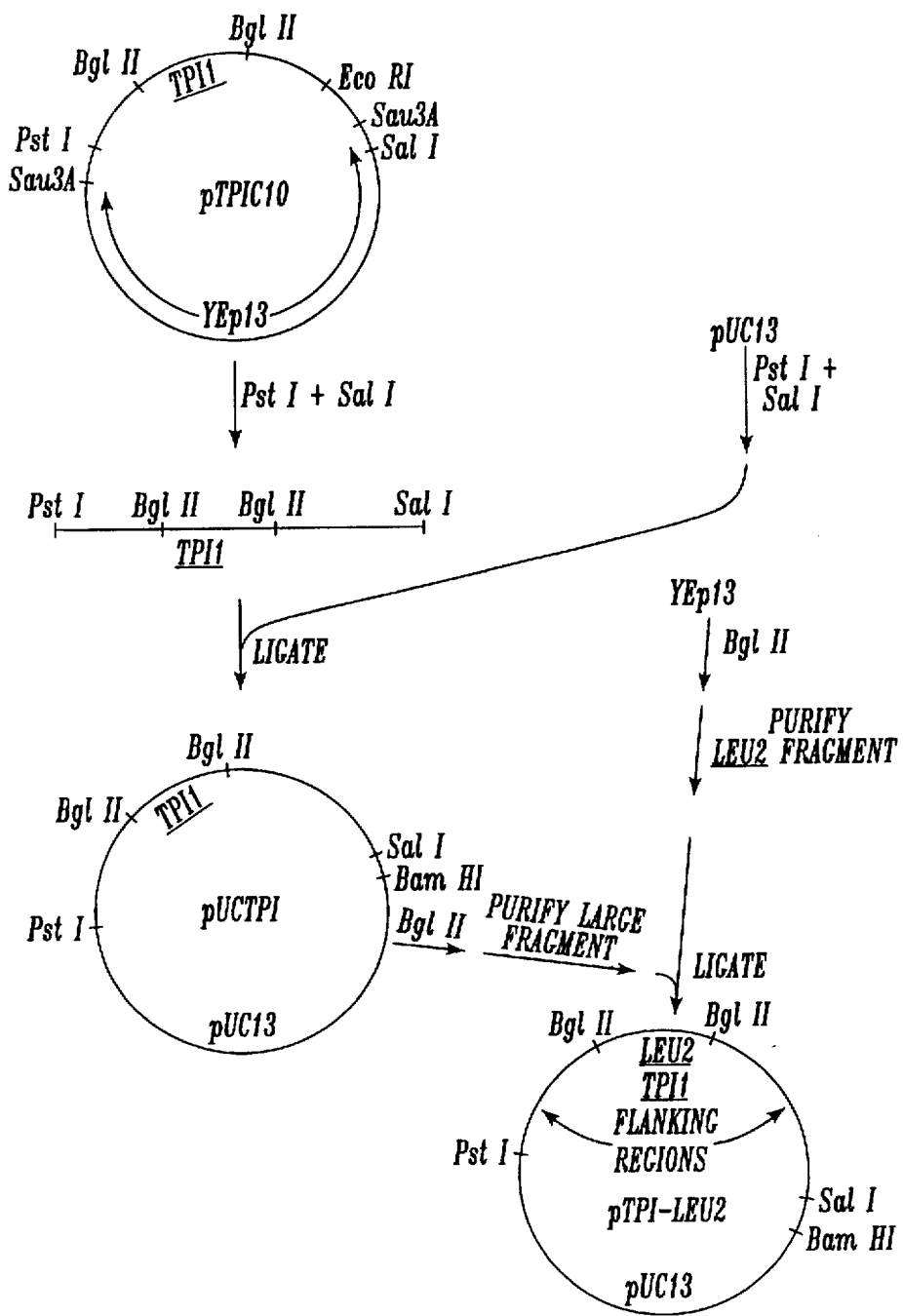

FIG. 8 illustrates the construction of the plasmid pTPI-LEU2.

FIG. 9 shows a portion of the polylinker sequence of plasmid pIC19R.

Figure 10:
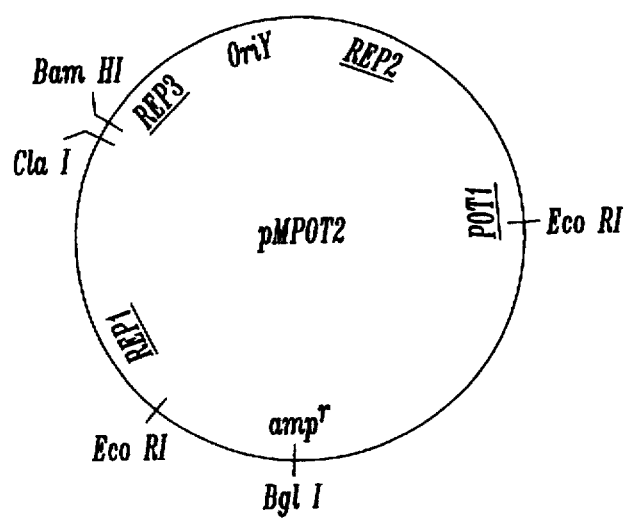

FIG. 10 illustrates plasmid pMPOT2.

Figure 11:
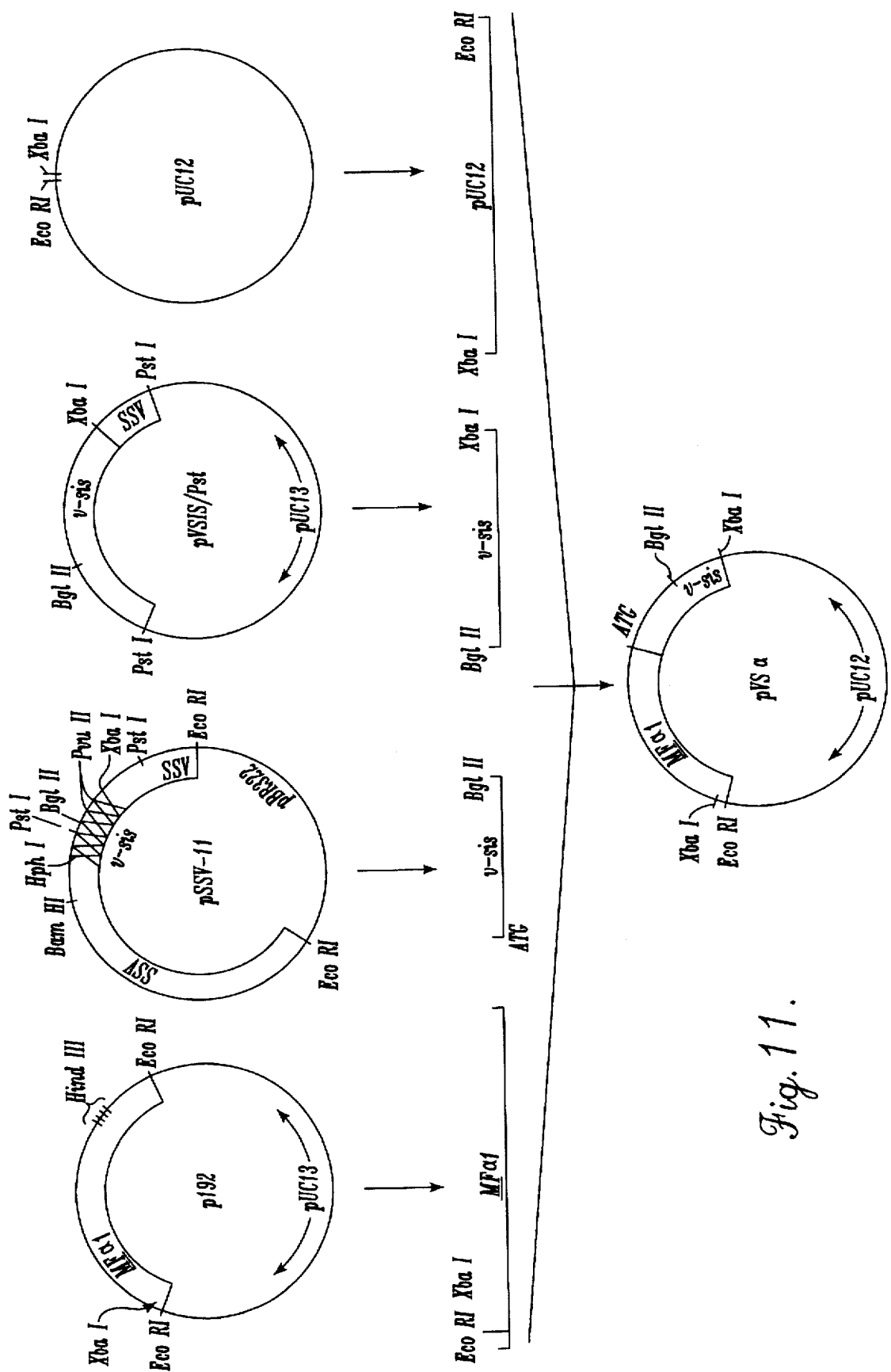

FIG. 11 illustrates the construction of the plasmid pVSα.

Figure 12:
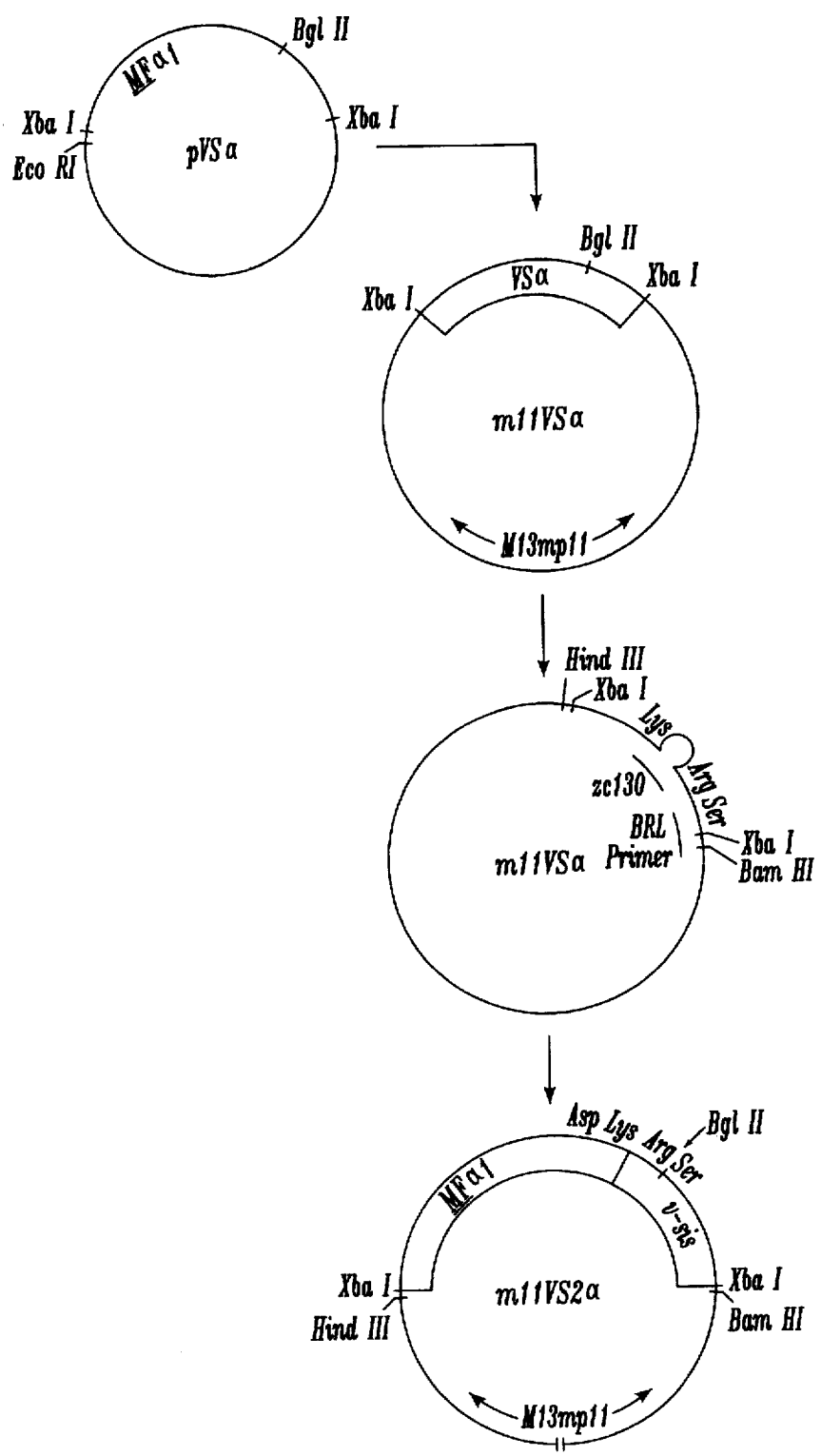

FIG. 12 illustrates the construction of the recombinate phage m11VS2α.

Figure 13:
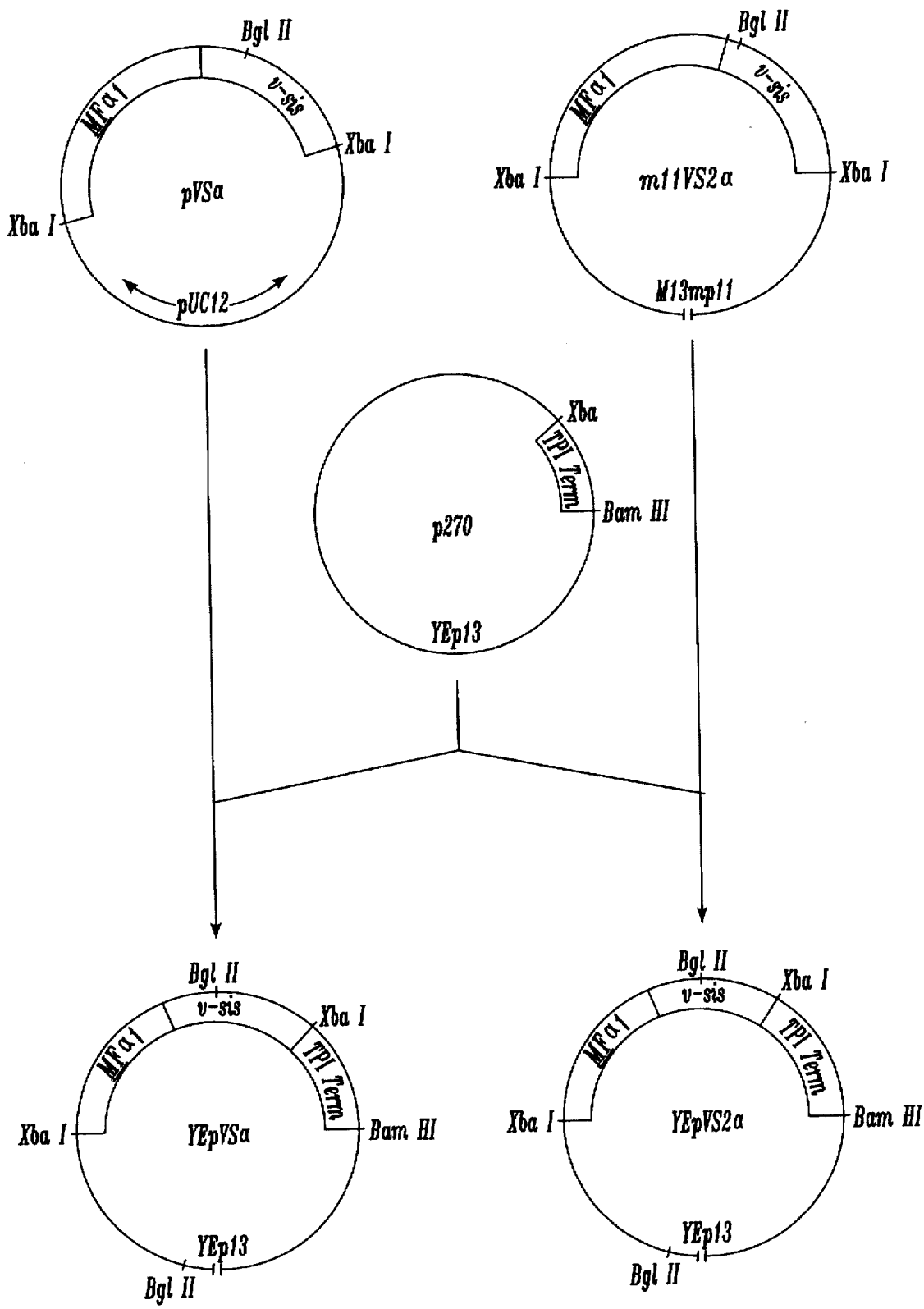

FIG. 13 illustrates the construction of the plasmids YEpVSα and YEpVS2α.

Figure 14:
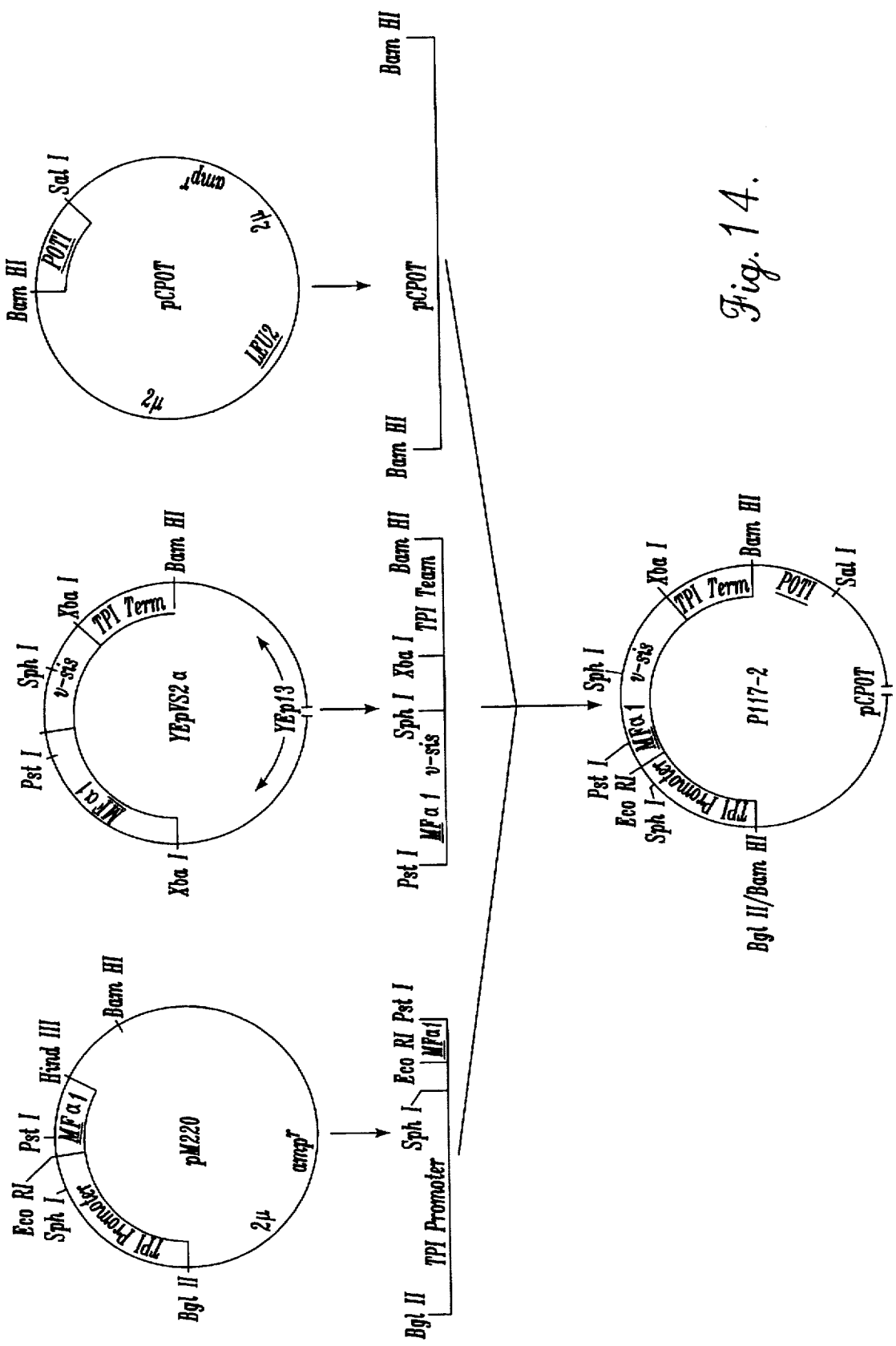

FIG. 14 illustrates the construction of the plasmid p117-2.

Figure 15:
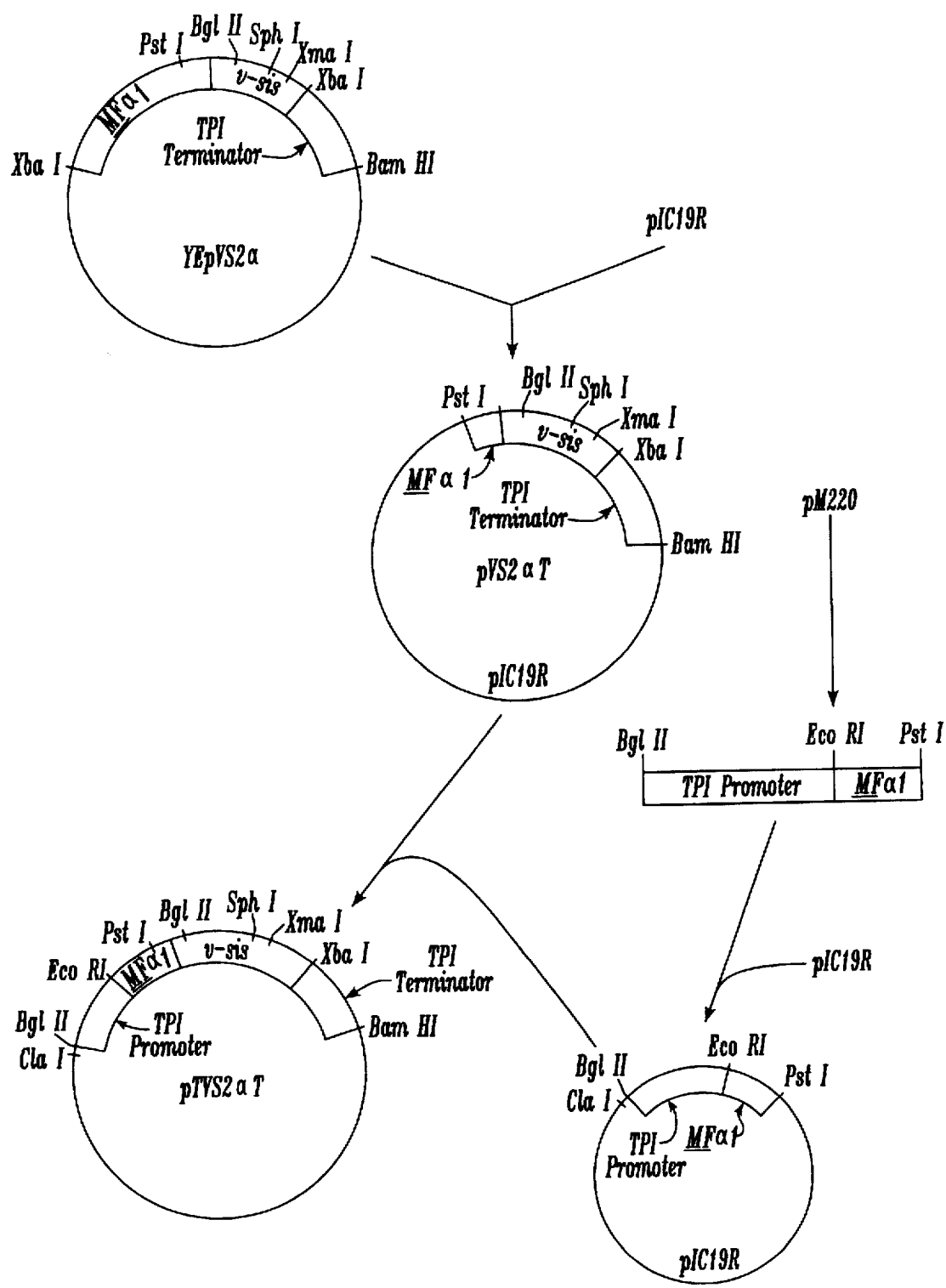

FIG. 15 illustrates the construction of the plasmid pTVS2αT.

Figure 16A:
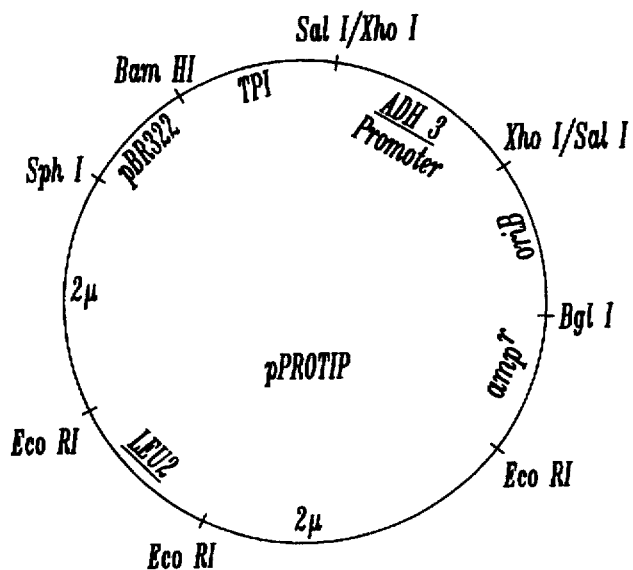
Figure 16B:
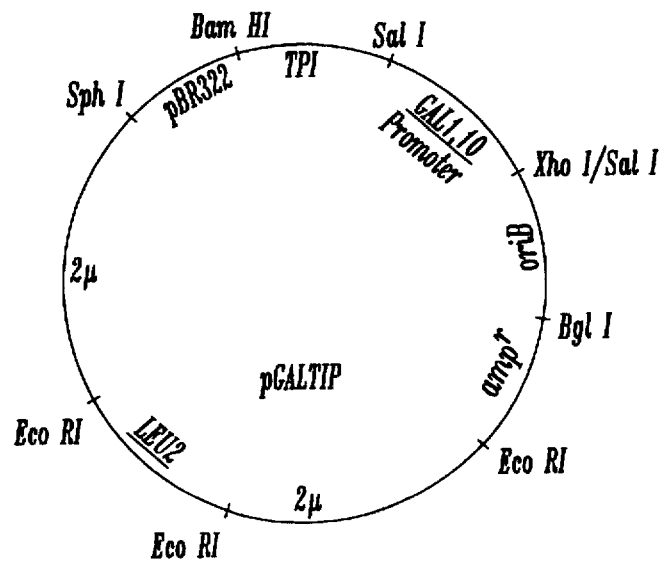

FIGS. 16A and 16B illustrate plasmids pPROTIP and pGALTIP.

Figure 17:
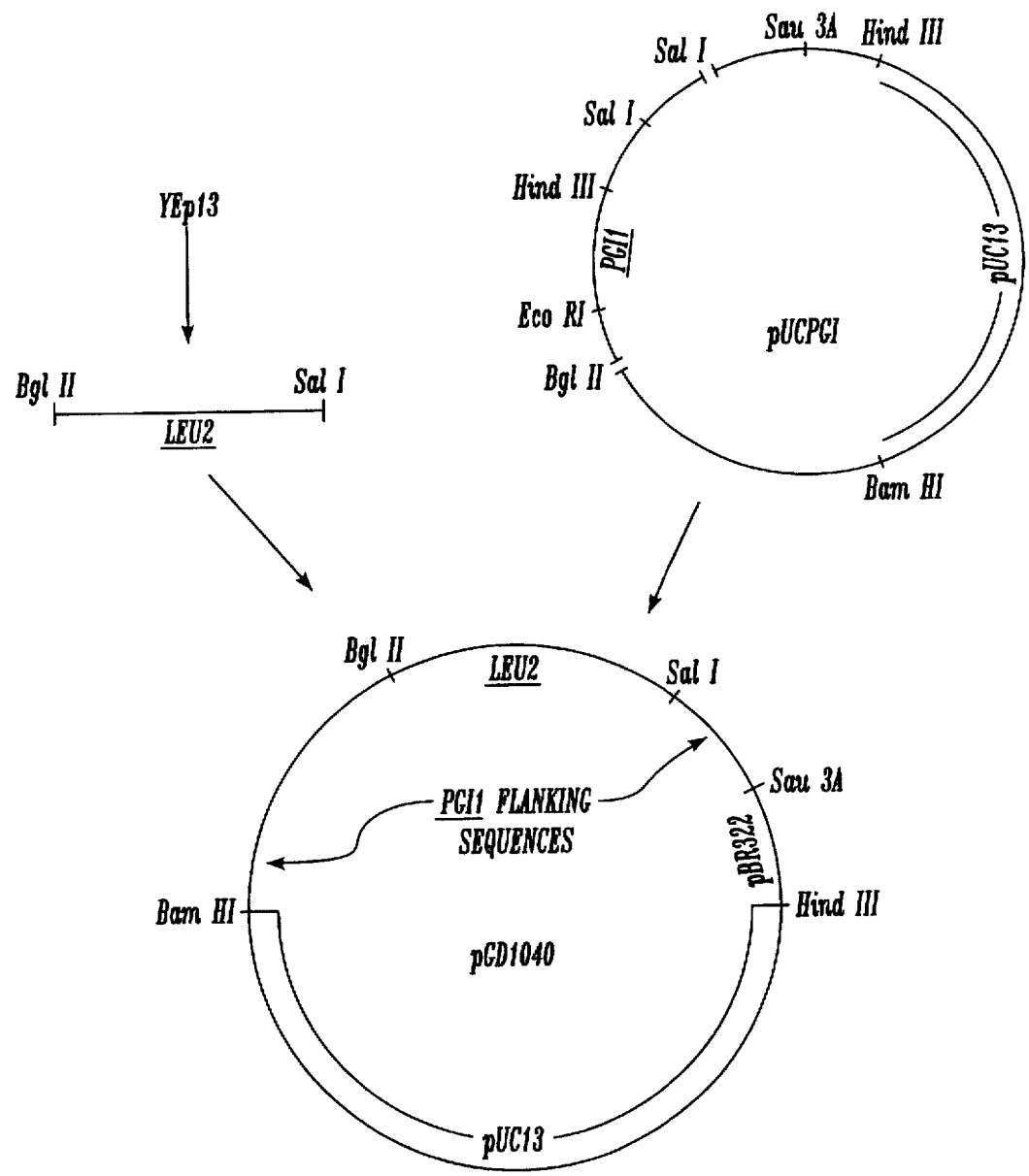

FIG. 17 illustrates the construction of plasmid pGD1040.

Figure 18:
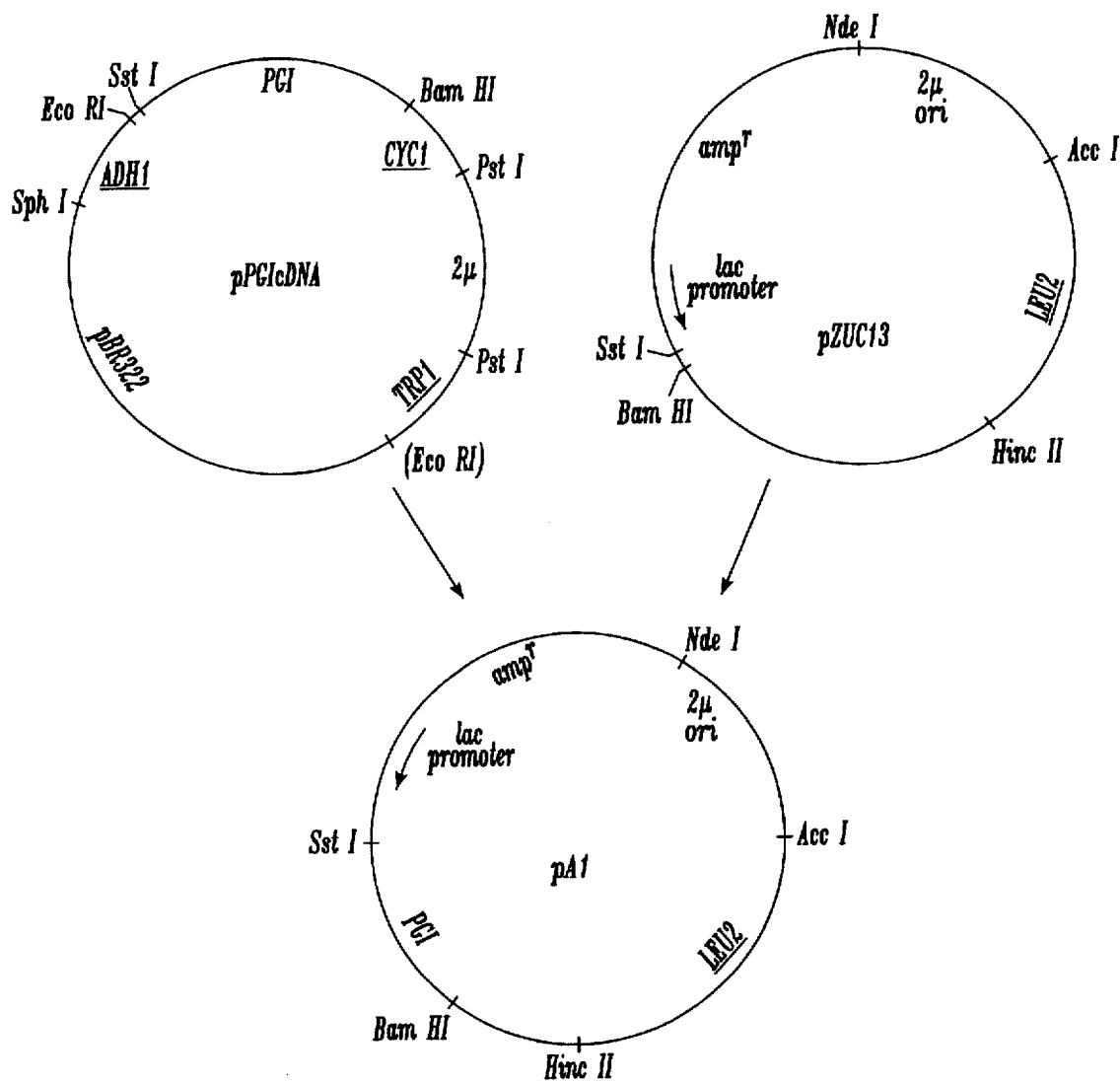

FIG. 18 illustrates the construction of plasmid pAL from pPGIcDNA and pZUC13.

Figure 19:
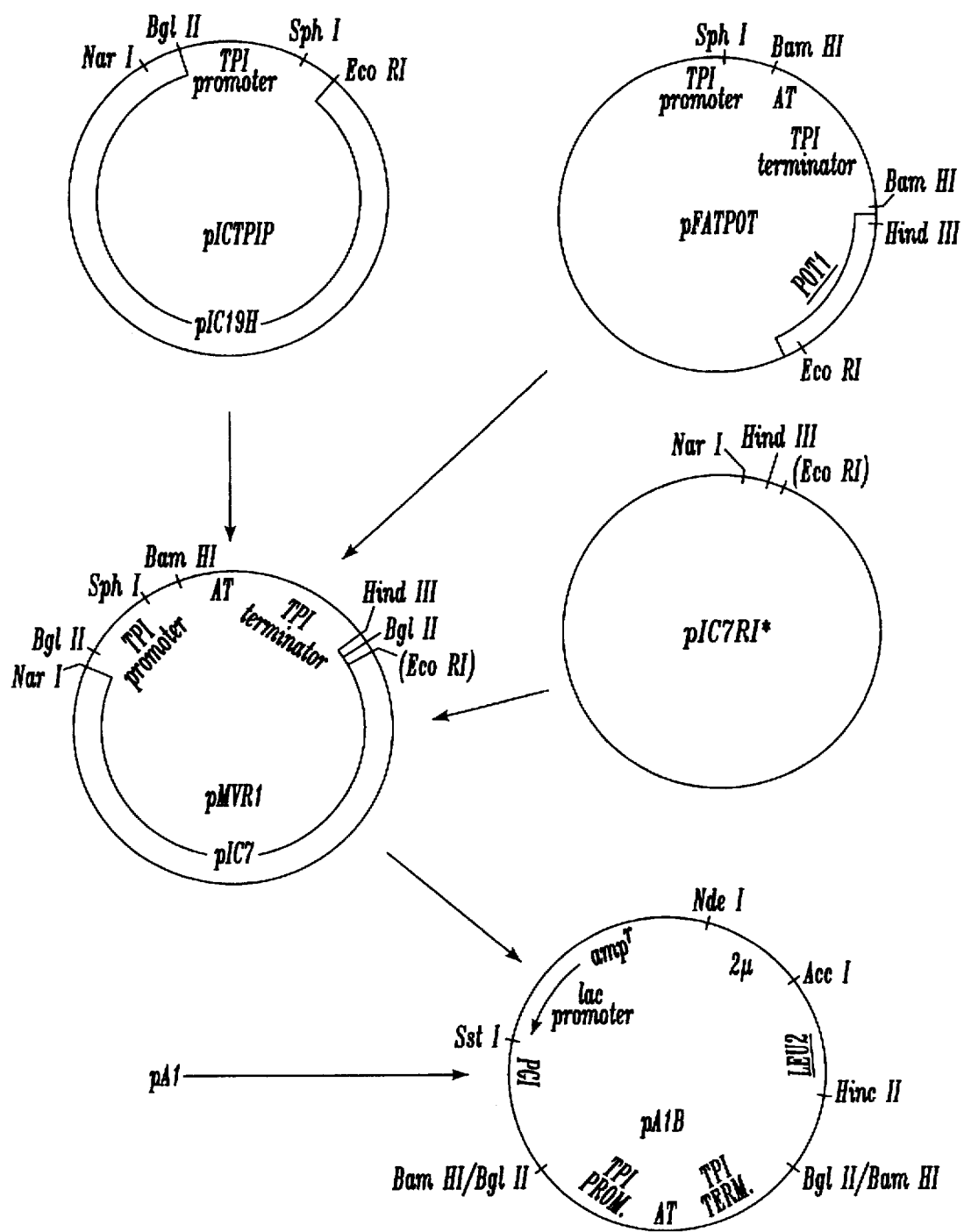

FIG. 19 illustrates the construction of plasmid pA1B.

DETAILED DESCRIPTION

The present invention is based in part upon the discovery that essential genes may be used as selectable markers on DNA constructs such as plasmids. An "essential gene" is defined as any gene that codes for a function necessary for cell viability or normal growth on complex media. Complex media are those media in which the nutrients are derived from products whose compositions are not well defined, such as crude cell extracts, meat extracts, fruit juice, serum, protein hydrolysates, etc. Hence, to select for a desired transformant according to the present invention, the growth medium will be merely a conventional complex growth medium, not a special medium containing a relatively expensive antibiotic, metal antagonist, or other agent lethal to the untransformed host cell, or medium lacking one or more specific nutrients required by the untransformed host. Essential genes include, but are not limited to, genes required for cell division, membrane biosynthesis, cell wall biosynthesis, organelle biosynthesis, protein synthesis, carbon source utilization, RNA transcription, and DNA replication.

A particular advantage of the present invention is that normal growth conditions for the host may be utilized to select for transformants, so that readily available and inexpensive complex media may be used and normal conditions may be used (optimal growth temperatures, etc.), all of which make it convenient and relatively inexpensive to select for desired transformants.

In order to use an essential gene as a selectable marker on a DNA construct, such as a plasmid, it is necessary to provide an appropriate mutant host cell strain. Using, for example, the one-step gene disruption method of Rothstein (*Meth. in Enzymology* 101:202-210, 1983), the co-transformation procedure described herein, suitable host strains may be constructed which carry deletions in an appropriate essential gene in the genome. Such deletion mutants grow when the mutation is complemented by a function coded by plasmid-borne genetic material. It is preferred that the deletions in the essential gene or genes of the genome of the host cell comprise substantial segments of the coding region and/or flanking regions. If the mutation or mutations in the essential gene are accomplished in a manner to achieve only point mutations, then there is a likelihood that the mutant host cell will revert to wild-type by reverse mutations, pseudo-reverse mutations, second site suppression, or a recombination repair mechanism, thereby reducing or eliminating the selectivity achievable by use of the plasmid-borne gene.

Essential genes often exist in multiple copies (such as histone or ribosomal RNA genes) and/or in multiple, related forms called gene families (such as different hexokinase genes, or different DNA polymerase genes). In such cases, these redundant functions may be sequentially mutated to make a host cell which is multiply deficient for a given essential function. However, by using a high copy number plasmid to increase the activity of the gene, a single essential gene on a plasmid may complement multiple host cell deficiencies. A high copy number plasmid is desirable because a concomitant increase in copy number of a cloned foreign gene may result in an increase in the production of the protein product encoded by said gene.

The selection for transformants containing high copy numbers of plasmids with essential genes may be accomplished by reducing the expression levels of each plasmid-borne essential gene and/or by reducing the activities of the gene products encoded by the plasmid-borne selectable marker. One approach is to mutate the plasmid-borne essential genes such that the transcription and/or translation rates of the genes are reduced or the gene products are altered to have lower specific activities. Another method for decreasing the expression levels of essential genes used as selectable markers is to use a gene from another organism to complement defects in the host cell. Such foreign genes may be naturally defective for expression in a host cell because the signals for transcription and/or translation may be sub-optimal in a different speckles or the gene product may have decreased activity because it is in a foreign cellular milieu.

A broad range of functions necessary for cell viability or normal growth on complex media exists. A defect or deletion in an essential gene may result in lethality, a decrease in the rate of cell division, cessation of cell division, termination of DNA, RNA, or protein synthesis, termination of membrane synthesis, termination of cell wall synthesis, termination of organelle synthesis, defects in sugar metabolism, etc. Examples of essential genes include the CDC (cell division cycle) genes of the yeast *Saccharomyces cerevisiae* (for review see Pringle and Hartwell, "The *Saccharomyces cerevisiae* Cell Cycle", in Strathern, et al., eds., *The Molecular*

Biology of the Yeast Saccharomyces Life Cycle and Inheritance, 97–142, Cold Spring Harbor, 1981), the genes coding for functions of the S. cerevisiae, E. coli, and mammalian cell glycolytic pathways, and the SEC (Novick and Schekman, Proc. Nat. Acad. Sci. USA 76:1856–1862, 1979 and Novick, et al., Cell 21:205–215, 1980) and INO (Culbertson and Henry, Genetics 80:23–40, 1975) genes of S. cerevisiae.

One preferred class of essential gene-deficient host cells is cells of the yeast S. cerevisiae containing defects in CDC genes known as cdc mutations, which lead to stage-specific arrests of the cell division cycle. Most cdc mutations produce complete blockage of events essential to the cell cycle by affecting either the synthesis or function of the particular CDC gene products. Such mutations may be identified by their effects on events which can be monitored biochemically or morphologically. Most known cdc mutations are conditionally lethal (i.e., temperature-sensitive) mutations, which result in the cessation of normal development of mutant cells grown under restrictive conditions. However, the primary defect resulting from a cdc mutation need not be a defect in a stage-specific function per se. For example, continously-synthesized gene products may have stage specific functions; a defect in the yeast glycolytic gene PYK1 (for the enzyme pyruvate kinase) is allelic to the cell division cycle mutation cdc19 (Kawasaki, Ph.D. Thesis, University of Washington, 1979). This mutation results in cell cycle arrest at the G1 phase of cells incubated in the typical yeast complex medium YEPD (1% yeast extract, 2% bactopeptone, and 2% dextrose). Thus, whether the cdc mutation results in a defect in a stage-specific function or whether it causes an inhibition or disabling mutation of a gene product having a stage-specific function, the effect of the defect may be monitored.

Pringle and Hartwell (ibid.) describe the function of some 51 CDC genes. For use in carrying out the present invention, such genes may be isolated from gene libraries by complementation in a strain carrying the desired mutation. Gene libraries may be constructed by commonly known procedures (for example, Nasmyth and Reed, Proc. Natl. Acad. Sci. USA 77:2119–2123, 1980; and Nasmyth and Tatchell, Cell 19:753–754, 1980). Strains carrying the desired cdc mutation may be prepared as described herein, or may be obtained from depositories accessible to the public, such as, the American Type Culture Collection and the Berkeley Yeast Stock Center.

A second preferred class of essential genes are those encoding products involved in the glycolytic pathway, including genes coding for metabolic enzymes and for regulatory functions. Examples of glycolytic pathway genes in S. cerevisiae which have been identified are the glycolysis regulation gene GCR1 and the genes coding for the enzymes triose phosphate isomerase, hexokinase 1, hexokinase 2, phosphoglucose isomerase, phosphoglycerate kinase, phosphofructokinase, enolase, fructose 1, 6-bisphosphate dehydrogenase, and glyceraldehyde 3-phosphate dehydrogenase. As noted above, the pyruvate kinase gene has been identified and described by Kawasaki (ibid., and U.S. Pat. No. 4,599,311) and by Burke et al., (J. Biol. Chem. 258:2193–2201, 1983). A plasmid containing a yeast phosphoglycerate kinase gene and accompanying regulatory signals has been described by Hitzeman, et al. (J. Biol. Chem. 225:12073–12080, 1980). Isolation and sequencing of the yeast triose phosphate isomerase gene TPI1 has been described by Alber and Kawasaki (J. Mol. Appl. Genet. 1:419–434, 1982) and by Kawasaki and Fraenkel (Biochem. Biophys. Res. Comm. 108:1107–1112, 1982). The gene for phosphoglucose isomerase (PGI1) has been cloned by Kawasaki and Fraenkel (ibid.).

A particularly preferred glycolytic gene is TPI1, which codes for the yeast triose phosphate isomerase, an enzyme which catalyzes the interconversion of glyceraldehyde-3-phosphate and dihydroxyacetone-3-phosphate and is therefore essential for glycolysis and gluconeogenesis. In S. cerevisiae the single genetic locus, TPI1, codes for this function. Cells carrying mutations in TPI1 do not grow on glucose and grow poorly on other carbon sources.

The S. cerevisiae TPI1 gene was isolated by complementation of the tpi1 mutation (Alber and Kawasaki, ibid., and Kawasaki and Fraenkel, ibid.). The triose phosphate isomerase gene from the fission yeast Schizosaccharomyces pombe (POT1) has been isolated by complementation of the same S. cerevisiae mutation and has been sequenced as shown in FIG. 5. Sequencing of the S. pombe gene, designated POT1, has demonstrated that the S. pombe TPI protein is homologous to the TPI protein of S. cerevisiae (Russell, Gene 40:125–130, 1985).

While in the usual case the essential gene which is utilized in the DNA construct (e.g., plasmid) will be a wild-type gene from the host species, in some cases it will be preferable to use an essential gene which is foreign to the host cell because the foreign gene may be naturally defective and thereby selectable to high plasmid copy number. As an example of such a foreign essential gene being used, the S. pombe POT1 gene may be effectively used as a selectable marker in an S. cerevisiae host.

Similarly, the Aspergillus nidulans TPI cDNA may be used as a selectable marker in a tpi⁻ strain of S. cerevisiae. In a manner analogous to the isolation of the S. pombe POT1 gene, the A. nidulans TPI cDNA was isolated on the basis of its ability to complement a deletion in the S. cerevisiae TPI1 gene.

Two characteristics of the A. nidulans TPI cDNA make it a preferred selectable marker on a yeast expression plasmid. First, the A. nidulans TPI sequence shares no significant homology with the S. cerevisiae genomic TPI sequence, which will prevent recombination between the plasmid and genomic sequences. Second, the heterologous TPI gene may be a defective gene in the yeast cell, thereby leading to an increase in copy number in order to produce more triose phosphate isomerase protein to complement the host cell deficiency.

In one embodiment, the A. nidulans TPI cDNA may be placed under the control of two different promoters in different yeast vectors. By using promoters of different strength or a repressible promoter such as the S. cerevisiae ADH2 or GAL1,10 promoters, expression levels of triose phosphate isomerase per plasmid can be varied. By regulating the amount of message produced, the plasmid copy number may be varied inversely with promoter strength; and the combined effects of promoter strength and copy number will produce message levels sufficient to complement the host cell TPI deficiency.

Another preferred selectable marker is the S. cerevisiae PGI1 (phosphoglucose isomerase) gene. The PGI1 gene was isolated by complementation of a pgi⁻ strain of S. cerevisiae. PGI1 can be used as a selectable marker in a host strain having a deletion in the genomic PGI1 locus.

The DNA constructs according to the present invention containing essential genes as selectable markers will be transformed into mutant host cells which are defective in the function of the essential gene. Properly mutated host cells must either be prepared or may be readily available from a public depository. Mutation of the wild-type cell may be accomplished according to conventional procedures. For example, wild-type cells may be treated with conventional mutagenizing agents such as ethane methyl sulfonate. The mutagenized Cells are then screened for the desired mutation by, e.g., growth deficiency on glucose. The mutants are then transformed with a plasmid containing an essential gene to identify the colonies where complementation occurs. Alternatively, the genome may be disrupted to create a specific mutation (for example, Rothstein, ibid.).

The stability of the plasmid containing the essential gene in the host cell may be dependent on the absence of homologous essential gene sequences in the host cell. The genetic defects in the host ensure that the plasmid will be maintained since growth of the host cell will not occur or will be severely limited by the lack of the essential gene function. Additionally, the integrity of the plasmid itself may be dependent upon the absence of homology between the plasmid-borne essential gene and the corresponding locus in the host genome, because recombination between respective plasmid and genomic loci may cure the cell of both the mutation and the plasmid. Thus, it is preferred that a mutation in the host cell genome which inactivates the genomic essential gene be of a substantial nature, i.e., deletions be made from the DNA sequences of the coding section and/or flanking regions of the chromosomal gene. Once this is accomplished, curing of the genomic mutation by recombination or gene conversion is less likely to occur.

The plasmids of the present invention are unexpectedly stable when maintained in the appropriate mutant host cells. A preferred host cell is yeast; however, other eukaryotic cells may be utilized, as well as prokaryotic cells. Host cells include, but are not limited to, Saccharomyces., Schizosaccharomyces, Aspergillus, E. coli, Bacillus, Kluyveromyces, Yarrowia, and cultured mammalian cells. In the case of yeast cells, the stability of the plasmids according to the present invention appears to exceed even that of yeast plasmids containing centromeres. Circular centromere plasmids are among the most stable plasmids previously reported for yeast, but suffer from an extremely low copy number (Clarke and Carbon, .ibid. and Stinchcomb, et al., 1982, ibid.). Linear centromeric yeast plasmids are either unstable or present at low copy number, depending on plasmid length (Murray and Szostak, ibid.). It is therefore an unexpected advantage that improved stability of plasmids bearing an essential gene is achieved.

The POT1, CDC4, PGI1, and A. nidulans TPI genes are examples of the utility of essential genes as selectable markers on expression vectors. These four genes belong to a broad class of genes that are required for cell proliferation on complex media. The use of other essential genes may allow for selection in plant or animal tissue culture which involves complex growth conditions. For example, a mammalian cell line defective for growth on a particular carbon source may be transformed with a yeast gene which complements the growth defect. At the extreme this may allow for the maintenance of plasmids in cells receiving nutrition from blood, serum, or sap of living animals or plants.

Data obtained from experiments using plasmids described herein show that human alpha-1-antitrypsin (AT) production is doubled by the use of the S. pombe POT1 gene as the selectable marker, when compared to AT production obtained with similar plasmids bearing a traditional auxotrophic selectable marker, LEU2. These results indicate that POT1 containing plasmids are functionally greater in copy number than the non-POT1 plasmids from which they are derived. Data also indicate that the use of other essential genes as selectable markers results in high plasmid copy numbers.

Data obtained for expression of the simian sarcoma virus v-sis gene show an approximately 5-fold to 8-fold increase in expression levels using POT1-containing plasmids as compared to results obtained with YEp13-derived vectors.

The techniques used to produce the DNA constructs, i.e., in particular the plasmids, according to the present invention, involve conventional methods. The essential gene to be utilized in the DNA construct may be isolated from a library by using a labeled DNA probe if the structure of the gene is known, or identified by ligating segments of the DNA library to conventional vectors, transforming the vectors into a mutant cell deficient in the particular essential gene and searching for colonies which are complemented. Once an appropriate DNA fragment containing the essential gene is identified it will be ligated to a vector which contains a DNA sequence coding for the structural protein which will be expressed. The essential gene may be utilized together with its own promoter and other controls necessary for expression within the host organism. Alternatively, a heterologous promoter may be utilized to increase or decrease expression of the essential gene. Methods of ligation of DNA fragments are amply described and are well within the skill of those of ordinary skill in the art to perform. The DNA coding sequence of the protein products to be expressed may be essentially that of any protein, particularly proteins of commercial importance, such as interferons, insulin, proinsulin, alpha-1-antitryopsin, growth factors, and tissue plasminogen activator.

After preparation of the DNA construct it will be transformed into the host organism under transforming conditions. Techniques for transforming prokaryotes and eukaryotes (including tissue culture cells) are known in the literature.

As described above the host organism must be deficient in the essential function for selection of the essential gene on a DNA construct. Mutant host strains are available from conventional depositories or may be made by conventional means from wild-types by mutagenesis and screening for the mutant carrying the proper mutation.

The transformed host may then be selected by growth on conventional complex medium. In the case of yeast, a conventional medium such as YEPD (1% yeast extract, 2% bactopeptone, and 2% dextrose) may be used. The selectable markers comprising essential genes according to the present invention may be used as markers wherever appropriate in any DNA construction and thus it will be recognized that constructs containing the essential gene selectable markers according to the present invention have many uses. The following examples are offered by way of illustration of such use, not by way of limitation.

Unless otherwise indicated, standard molecular biology methods were used. Enzymes were obtained from Bethesda Research Laboratories, New England BioLabs, and Boehringer Mannheim Biochemicals, and were used as directed by the manufacturer or as described by Maniatis, et al. (*Molecular Cloning*: A *Laboratory Manual*, Cold Spring Harbor Laboratory, 1982). *E. coli* cultures were transformed by the calcium chloride method, also disclosed in Maniatis, et al. (ibid.). Yeast cultures were transformed by the method of Beggs (*Nature* 275:104–108, 1978), with modifications as described herein.

EXAMPLE 1

The S. cerevisiae CDC4 gene as selectable marker

A. Construction of a stable CDC4-containing plasmid

A yeast genomic library was constructed by partial digestion of yeast DNA with Sau3A, size selection on sucrose gradients, and insertion of the selected fragments into the yeast vector YRp7 which had been digested with BamHI (Nasmyth and Reed, *Proc. Natl. Acad. Sci. USA* 77:2119–2123, 1980). A recombinant plasmid containing the CDC4 gene was isolated by transformation of yeast strains GEB5 (MATa cdc4-4 leu2 trp1 lys1 ura1) and GEB7 (MATa cdc4-3 leu2 trp1 lys1) with the library. These strains were derived from strains A364A cdc4-3 and A364A cdc4-4 (Hartwell, et al., *Genetics* 74:267–286, 1973) by crossing with a strain known to transform at high frequency (K79 [MATα leu2 trp1]) (Nasmyth, et al., *Nature* 289:244–250, 1981; Tatcheil, et al., *Cell* 27:25–35, 1981) followed by backcrossing to high transforming strains (K79 and K80 [MATα leu2 trp1 lys1]) to obtain the cdc4-3 and cdc4-4 mutations in the desired genetic background (leu2 trp1). Selection of transformants for tryptophan prototrophy and the ability to grow at the restrictive temperature (37°) identified one such plasmid (designated pJY35) which was shown to integrate into the genome and map to the CDC4 locus. Spontaneous plasmid integrants were identified on the basis of their selective growth advantage. This growth advantage is due to the presence, on the original plasmid, of a CDC4-linked gene which is deleterious to cell growth when present at high copy number (i.e., when the plasmid is not integrated into the host genome). In the integrants, the TRP1 plasmid marker was shown to be genetically linked to SUP11, which is linked to CDC4 on chromosome VI (Mortimer and Schild, "Genetic Map of *Saccharomyces cerevisiae*" in Strathern, et al., eds., *The Molecular Biology of the Yeast Saccharomyces cerevisiae Life Cycle and Inheritance*, 641–651, cold Spring Harbor, 1981). The cdc4-3 complementing region was purified from pJY35 as a 6.4kb BamHI fragment and was joined, using T4 DNA ligase, to the vector YRp7 (Struhl, et al., *Proc. Natl. Acad. Sci. USA* 76:1035–1039, 1979) which had been cleaved with BamHI. This construct is known as pJY51, and is illustrated in FIG. 1.

Figure 1:
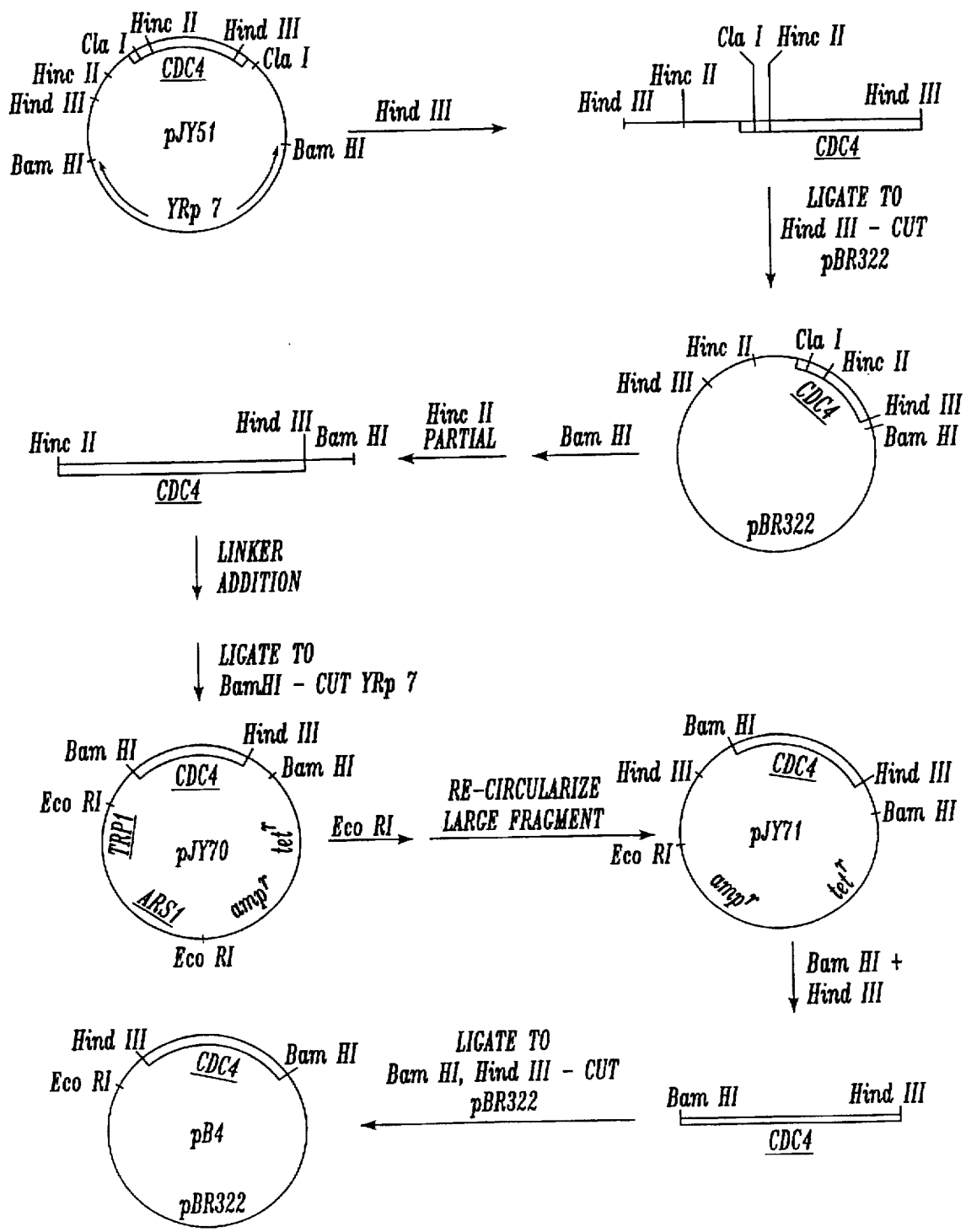
FIG. 1 illustrates the construction of plasmid pB4.

Referring to FIG. 1 the CDC4 coding region was purified away from flanking genomic DNA sequences in the following manner. Plasmid pJY51 was cleaved with HindIII and the 3.6 kb fragment comprising the CDC4 region was subcloned in the bacterial plasmid pBR322. This construct was digested to completion with BamHI, partially digested with HincII, and the ca. 2.3 kb CDC4-containing fragment was purified. The HincII fragment end was converted to a BamHI end by the addition of linker sequences (sequence:5'CCGGATCCGG3') (obtained from Collaborative Research and subsequent digestion with BamHI to remove excess linkers. The resulting fragment, comprising approximately 1.9 kb of the CDC4 gene, was inserted into the BamHI site of YRp7 to produce plasmid pJY70. This plasmid was shown to complement the cdc4-3 mutation as described above. Although the 1.9 kb fragment lacks small portions of both the 5'- and 3'-coding regions of the CDC4 gene, it surprisingly complements the temperature-sensitive defect. Presumably, transcription and translation of the CDC4 sequence is controlled by sequences located in the pBR322 regions of the plasmid, allowing for production of a functional gene product.

Plasmid pJY70 was cleaved with EcoRI to remove the yeast TRP1 and ARS1 sequences and was re-ligated, yielding a hybrid plasmid comprising pBR322 and CDC4 sequences. This plasmid is known as pJY71, and is illustrated in FIG. 1.

The 1.9 kb yeast sequence was purified from pJY71 as a BamHI-HindIII fragment. This fragment was joined to pBR322 which had been linearized by digestion with BamHI and HindIII, to produce the plasmid pB4, and is illustrated in FIG. 1.

Figure 2:
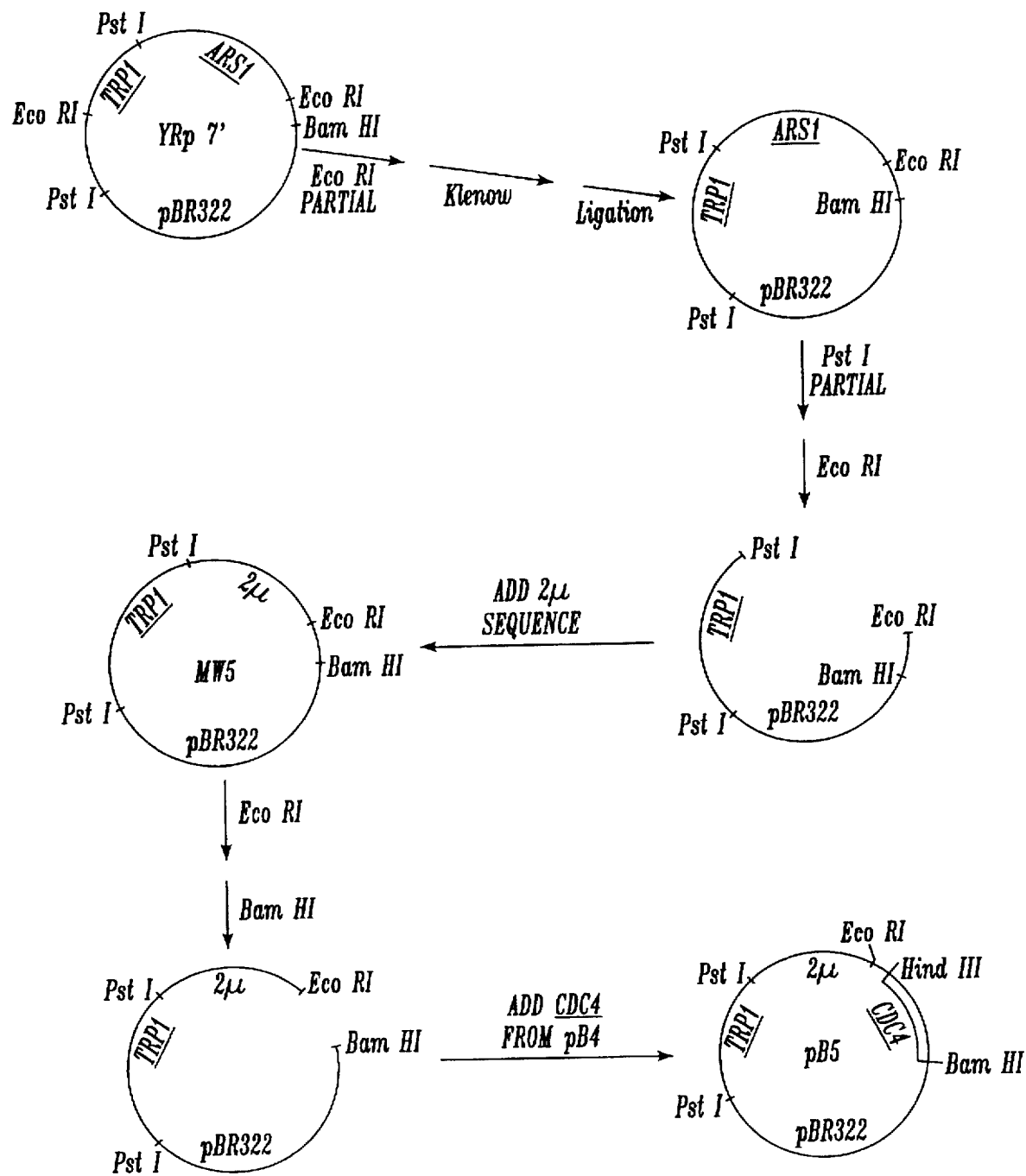
FIG. 2 illustrates the construction of plasmid pB5.

The CDC4 region was re-isolated from pB4 for insertion into a high copy number yeast vector. Such a vector will contain an origin of replication of the yeast 2μ plasmid, and one or more restriction enzyme cleavage sites which will serve as cloning sites for foreign genes of interest. Preferably such sites will be unique sites on the plasmid. A preferred vector is MW5, which comprises the yeast 2μ plasmid replication origin and unique EcoRI and BamHI cloning sites. Referring to FIG. 2 plasmid MW5 was derived from plasmid YRp7' (Stinchcomb, et al., *Nature* 282:39–43, 1979) by partial digestion with EcoRI to cleave, on average, one of the two EcoRI sites per molecule. The resulting unpaired ends of the linear molecules were filled in using DNA polymerase I (Klenow fragment) and the resulting blunt ends were re-joined using T4 DNA ligase. The resulting plasmid which retained the EcoRI site adjacent to the ARS1 sequence was then selected. The ARS1 sequence was removed by digestion with PstI and EcoRI, and replaced with the PstI-EcoRI fragment of plasmid YEp13 (Broach, et al., *Gene* 8:121–133, 1979) which comprises the replication origin of yeast 2μ DNA. The resulting plasmid, designated MW5, is illustrated in FIG. 2.

To construct the final CDC4-containing stable plasmid, MW5 was cleaved with EcoRI and BamHI. The CDC4 fragment was purified from plasmid pB4 by digesting the plasmid with BamHI and EcoRI. The two fragments were joined, using T4 DNA ligase, and the chimeric molecules so produced were transformed into *E. coli* strain RRI (Nasmyth and Reed, ibid.) with selection for ampicillin-resistant, tetracycline-sensitive colonies. Plasmid pB5 (shown in FIG. 2), isolated from one such colony, comprises the yeast 2μ replication origin, pBR322 plasmid sequences, the selectable marker TRP1, 1.9 kb of the yeast CDC4 coding sequence, and a unique EcoRI cloning site.

B. Construction of a plasmid for disruption of host CDC4 gene

The stability, in a transformed host, of the CDC4-containing plasmid according to the present invention is dependent on the lack of a functional CDC4 gene in the host. It is further desirable that no homology exists between the host genome and the CDC4-containing stable plasmid in order to prevent recombination between plasmid and chromosomal DNA's. To obtain a yeast strain having a suitably deleted CDC4 locus, a yeast host containing the wild-type CDC4 gene may be transformed with a linearized plasmid fragment having a "disrupted" CDC4 gene (Rothstein, ibid.). The linearized plasmid fragment is a preferred transforming agent because the free ends of the fragment may enhance recombination within the CDC4 region. Such a plasmid fragment will have intact CDC4 flanking regions at its ends to facilitate recombination with the intact genomic CDC4 locus. The genetic material inserted between the CDC4 flanking regions of the plasmid fragment will code for a phenotypic characteristic which can be selected in the transformed host (a selectable marker such as TRP1 or LEU2). The disrupting plasmid will preferably also lack a yeast origin of replication in order to select for the integration of the disrupted CDC4-selectable marker sequence into the host genome. Following transformation with the linearized plasmid, genetic recombination results in the substitution of the disrupted sequence for the genomic sequence of the host. Cells in which the CDC4 gene has now been deleted are then selectable according to the marker used in the disruption.

A method for a one-step disruption of a host genome is described by Rothstein (ibid.). As described above, disruption is performed with the added improvement of co-transforming a host strain with an intact stable plasmid and a linearized plasmid such that in addition to achieving disruption of the host genome, transformation of the host with the stable plasmid is also effected.

A preferred plasmid for disruption of the host CDC4 locus is pB15L, shown in FIG. 3. It comprises the yeast LEU2 gene inserted between the flanking regions of CDC4, and the vector pUC13 (Vieira and Messing, *Gene* 19:259–268, 1982 and Messing, *Meth. in Enzymology* 101:20–77, 1983). When linearized at the junctions of yeast and vector sequences and transformed into a suitable yeast host strain, the plasmid produces a deletion of CDC4 in the host genome resulting from the substitution of the LEU2 sequence for the CDC4 region. In a host strain auxotrophic for leucine, disrupted transformants may then be selected on the basis of leucine prototrophy.

To construct plasmid pB15L, a 6.4 kb fragment comprising the CDC4 gene and its 5'- and 3'-flanking regions was purified from a BamHI digest of pJY51. This fragment was inserted into BamHI-digested pUC13 to produce the plasmid pB14. Most of the CDC4 coding region was removed by digesting pB14 with ClaI and purifying the larger fragment which comprises the pUC13 and CDC4 flanking sequences. The fragment ends were modified by the addition of XhoI (BglII) "smart" linkers (Worthington Diagnostic), and the 2.8 kb BglII LEU2 fragment of YEp13 (Broach, et al., *Gene* 8:121–133, 1979) was joined to the resultant cohesive termini. DNA so prepared was used to transform *E. coli* strain RRI. Transformants were selected on the basis of leucine prototrophy, since the yeast LEU2 sequence complements the leuB defect in the *E. coli* host. Plasmid pB15L was purified from one such transformed colony.

Plasmid PB15L comprises only about 50 base pairs of the 5' end of the CDC4 coding sequence in addition to the 5' and 3' flanking sequences. A comparison of the maps of plasmids pB5 and pB15L shows a lack of homology between their respective CDC4 sequences as the junction points of the CDC4-LEU2 gene fusion of pB15L are located outside the region of the CDC4 fragment present in pB5. This lack of homology prevents recombination between pB5 and the disrupted CDC4 locus in the host cell.

C. Co-transformation of *S. cerevisiae*

To simultaneously delete the genomic CDC4 gene and introduce plasmid pB5, yeast cells were co-transformed with BamHI-cleaved pB15L and intact plasmid pB5. The host strain to be used in the transformation should be auxotrophic for tryptophan and leucine in order to select simultaneously for plasmid pB5 and the genomic CDC4 disruption. Strain A2.7.c (MATα cdc4-3 trp1 leu2-2,112 lys1 his3-11,15 can1) obtained from a cross of strain A2 (MATα leu2-2,112 his3-11,15 can1; see Szostak, *Meth. in Enzymology* 101:245–252, 1983) with strain GEB7 (see Example 1A) was used.

In a typical co-transformation experiment, 10 ml of a culture of *S. cerevisiae* A2.7.c in log phase growth were transformed with approximately 6 µg of BamHi-digested pB15L, 1 µg pB5, and 10 µg calf thymus DNA as carrier. Transformation conditions were as described by Beggs (ibid.). Cells were plated on a medium lacking leucine and tryptophan. They were grown overnight at 22° and shifted to 37°. Approximately 30 colonies were obtained. The control transformation with pB5 alone and selection for tryotophan prototrophy produced approximately 1,000 transformants.

Six co-transformed colonies were analyzed to verify the disruption of the CDC4 locus and to test the stability of the pB5 plasmid. Genomic DNA was isolated from co-transformants by the method of Abraham, et al. (*Cold Spring Harbor Symposium Quant. Biol.* 47:989–998, 1983) and was digested with EcoRI and BamHI, electrophoresed on an agarose gel, and transferred to nitrocellulose (Southern *J. Mol. Biol.* 98:503–517, 1975). The blot was probed with the 2.5 kb BamHI-HindIII fragment from the 5' flanking region of CDC4 present in pB15L but absent from pB5. FIG. 4 shows that the probe hybridized to a 6.4 kb fragment of DNA from untransformed cells (lane b); there is no EcoRI site within this 6.4 kb BamHI fragment. As the LEU2 sequence contains an EcoRI site, disruption of the CDC4 locus will result in a reduction in size of the hybridizing band (indicated by arrows in FIG. 4). This is the case for the transformants represented in lanes c, d, f, g, and h. Lane e shows a somewhat different pattern and retains the genomic-size band, indicating that deletion of the genomic CDC4 did not occur. (The smaller bands seen in lanes c through h are due to contamination of the gel-purified probe, as shown by the patterns of the controls in lanes a and b.)

The six co-transformants were tested for plasmid stability by growing on complex medium (YEPD). Cells were plated on YEPD at 25°, and replica plated onto YEPD at 37°, tryptophanless medium, and leucineless medium. Results summarized in Table 1 indicate that all co-transformants except #3 were 100% stable for the plasmid markers on complex media. (Isolate number 3 is the same co-transformant represented in lane 3 of FIG. 4).

Further stability tests were performed on two co-transformants, numbers 1 and 2. Testing was performed on 63 and 681 colonies respectively. After growth for 30 generations on YEPD at 30°, all colonies were prototrophic for tryptophan and leucine.

Co-transformant #1 was tested for growth rate at 22° and was found to grow at the same rate as an untransformed A2.7.c control.

Co-transformant #1 has been designated BELL1. It has been deposited with ATCC under accession number 20698.

TABLE 1

STABILITY OF CDC4 PLASMIDS

| Isolate Number | Total Colonies[a] | CDC4+[b] | Trp+[c] | Leu+[d] |
|---|---|---|---|---|
| 1(BELL 1) | 123 | 123 | 123 | 123 |
| 2 | 80 | 80 | 80 | 80 |
| 3 | 83 | 80 | 80 | 83 |
| 4 | 96 | 96 | 96 | 96 |
| 5 | 88 | 88 | 88 | 88 |
| 6 | 115 | 115 | 115 | 115 |

[a]Cells were plated on complex medium (YEPD) at 25° and allowed to grow for 30 generations.
[b]Cells were replica plated to YEPD at 37° and allowed to grow for 30 generations. Cells lacking an intact CDC4 gene failed to grow at this (restrictive) temperature.
[c]Cells were replica plated to medium lacking tryptophan and counted after 30 generations.
[d]cells were replica plated to medium lacking leucine and counted after 30 generations.

EXAMPLE 2

Schizosaccharomyces pombe POT1 gene

A. *S. pombe* POT1 gene as a selectable marker

The *Saccharomyces cerevisiae* TPI1 gene codes for the triose phosphate isomerase protein and has been obtained by complementing the tpi1 deficiency (Kawasaki and Fraenkel, ibid.; Alber and Kawasaki, ibid.). Surprisingly, the homologous gene from *S. pombe* has been isolated by complementing the same *S. cerevisiae* tpi1 mutation. The *S. pombe* TPI gene, designated as POT1 (for *pombe triose* phosphate isomerase), has been cloned from a library described by Russell and Hall (*J. Biol. Chem.* 25:143–149, 1983) which contains genomic *S. pombe* DNA that has been partially digested with Sau3A and inserted into the vector YEp13. A preliminary DNA sequence (by the method of Maxam and Gilbert, *Meth. in Enzymology* 65:497–559, 1980) has demonstrated that the POT1 gene codes for the TPI protein and said protein is homologous with TPI proteins from other organisms (see Alber and Kawasaki, ibid.). This POT1 DNA sequence is given in FIG. 5, together with the *S. cerevisiae* TPI1 DNA sequence and the respective inferred protein sequences.

The *S. pombe* POT1 gene is preferred in this example over the *S. cerevisiae* TPI1 gene as a selectable marker in *S. cerevisiae*. Foreign genes, such as POT1 in *S. cerevisiae*, may not function well in an alien host cell and therefore may necessitate a higher copy number to complement a host cell defect. Also the selectable POT1 gene on a yeast plasmid allows for the use of the endogenous TPI1 promoter and TPI1 terminator (control regions that show no homology with POT1) for expression of commercially important genes on the same vector. Because POT1 and the flanking regions of TPI1 show no homology, intramolecular recombination and subsequent plasmid instability are reduced. Finally, the POT1 gene is not likely to recombine with the *S. cerevisiae* chromosomal DNA because it shares little homology at the DNA level with the TPI1 sequence and much of the TPI1 gene has been deleted in the host strains. Thus, POT1 containing plasmids may remain at high copy numbers which are desirable for the elevated expression of foreign genes of commercial interest in yeast.

A plasmid comprising the POT1 gene was identified from the *S. pombe* library of Russell and Hall (ibid.) by complementation of the tpi1 mutation in *S. cerevisiae* strain N587-2D (Kawasaki and Fraenkel, ibid.).

A restriction map of this plasmid, pPOT, is depicted in FIG. 6. Because pPOT contains the vector YEp13, it is inherently unstable, since it lacks replication functions necessary for the maintenance of 2-micron plasmids in yeast. Therefore, the POT1 gene may be moved into more competent vectors, such as C1/1 and related vectors that contain the entire 2-micron plasmid sequences. Plasmid C1/1 was derived from pJDB248 (Beggs, *Nature* 275:104–109, 1978) and pBR322 as described in Example 3 herein. It contains all of the yeast 2-micron plasmid DNA, a selectable LEU2 gene, and pBR322 sequences.

The POT1 gene was isolated from pPOT as a BamHI-XbaI restriction fragment of nearly 3,400 base pairs and was inserted into the corresponding polylinker sites of pUC13. The resulting plasmid is pUCPOT, a partial restriction map of which is shown in FIG. 6.

The pUCPOT plasmid was cut with SalI and religated to delete about 1,800 base pairs of *S. pombe* and *S. cerevisiae* DNA. This resulting pUCPOT-Sal plasmid is illustrated in FIG. 6.

The POT1 gene Was put into C1/1 in the following manner. As both C1/1 and pUCPOT-Sal have a BglI site in the ampicillin resistance gene and a unique BamHI site at some other location, the POT1 fragment of pUCPOT-Sal may be substituted for a portion of the pBR322 region of C1/1. C1/1 was cut with BglI and Bam HI to liberate a large fragment of nearly 7,700 base pairs that contains part of the amp$^r$ gene, all 2-micron DNA, and the LEU2 gene. Likewise, pUCPOT-Sal was cut with BglI and BamHI to liberate a fragment of nearly 3,400 base pairs that contains the other portion of the amp$^r$ gene and the POT1 gene. These two fragments were ligated to form pCPOT, which contains a "restored" selectable amp$^r$ gene, the POT1 gene, the LEU2 gene, all 2-micron DNA, and the bacterial origin of replication region from pUC13 (the bacterial origin region from pUC13 allows for a higher copy number of plasmids in *E. coli* than does the origin region of pBR322).

*E. coli* strain HB-101 transformed with pCPOT has been deposited with ATCC under accession number 39685.

The POT1 gene may also be inserted into C1/1-derived vectors by a similar construction. For example, the plasmid pFAT5 (FIG. 7) contains an expression unit for the production of human alpha-1-antitrypsin (AT) inserted into C1/1. This expression unit, prepared as described in Example 4 consists of the TPI1 promoter, the AT cDNA sequence, and the TPI1 transcription terminator. A restriction map of pFAT5 is given in FIG. 7.

pFAT5 was cut with BglI and BamHI to liberate a fragment (2,200 base pairs) that contains the AT gene and the TPI1 terminator. Also liberated is a BglI-BamHI fragment which is identical to the C1/1 BglI-BamHI fragment described above, except that the fragment from pFAT5 contains an additional 900 base pairs that comprise the TPI1 promoter. This latter pFAT5 piece and the pUCPOT-Sal 3400 bp BGII-BamHI fragment (described above) are ligated to form the plasmid pFPOT, which has the restriction map shown in FIG. 7.

The vector pFPOT was cut at the unique BamHI site to allow for the insertion of the 2,200 base pair AT gene and TPI1 terminator fragment from pFAT5. The cloning of the 2,200 base pair fragment in the proper orientation into pFPOT allows for the expression of human AT in this yeast vector. The properly ligated product is designated pFATPOT, whose restriction map is given in FIG. 7.

B. Disruption of host TPI gene

The *Saccharomyces cerevisiae* TPI1 gene has been cloned and sequenced (KaWasaki and Fraenkel, ibid. and Alber and Kawasaki, ibid.). The plasmid pTPIC10, comprising the structural gene for the TPI protein, has been described in Alber and Kawasaki (ibid.). A BglII site exists at DNA position 295 in the coding region of TPI1, and another BglII site is located approximately 1,200 base pairs away in the 5' flanking region. These BglII sites are convenient cloning sites for deleting part of the TPI1 gene and for inserting another gene, such as the yeast LEU2 gene. Such a construct can be used to produce a disruption of the genomic TPI1 locus in a transformed host.

At approximately −1800 in the 5' flanking region of TPI1 is a PstI site. In pTPIC10, therefore, the TPI1 gene is flanked by a PstI site on the 5' side and by a SalI site (in the tet$^r$ gene) on the 3' side. This PstI-SalI fragment which contains TPI1 was inserted into pUC13 at the PstI and SalI sites to produce pUCTPI. A restriction map of the PstI-SalI insert (into pUC13) is given in FIG. 8.

The plasmid pUCTPI was then cut with BglII and the two DNA fragments were separated by electrophoresis. The larger fragment was purified and phosphatased to prevent self-ligation. Into the BglII sites of this DNA was ligated the yeast LEU2 gene, which was removed from the plasmid YEp13 (Broach, et al., *Gene* 8:121–133, 1979) as a BglII fragment. The resulting plasmid was pUCTPI-LEU2, which carries a partial deletion of TPI1 and an insertion of LEU2. pUCTPI-LEU2 is depicted in FIG. 8.

The plasmid pUCTPI-LEU2 was cut with PstI and BamHI to linearize the DNA. The yeast sequences by electrophoresis and gel purification. The yeast DNA portion depicted in FIG. 8 was used to transform *S. cerevisiae* strain E2-7B (ATCC No. 20689), which is deficient for LEU2, in order to "disrupt" the TPI1 chromosomal gene (Rothstein, ibid.). Leu$^+$ transformants were selected on a synthetic (modified Wickerham's) medium (Mortimer and Hawthorne, in Rose and Harrison, eds., *The Yeasts* vol. 1, 385–460, Academic Press, 1969) which contained 3% glycerol and 1% lactate (neutralized to pH 7), 1M Sorbitol, and no leucine. The transformants were screened for a TPI deficiency by their inability to grow on YEP-Dextrose. One tpi$^-$ transformant was found among the first 99 transformants screened. This strain was designated as E2-7BΔtpi#29 (hereinafter Δtpi#29). Δtpi#29 grew on YEP-3% Glycerol-1% Lactate but not on YEP-Dextrose. Enzyme assays (Clifton, et al., *Genetics* 88:1–11, 1980) were run on crude cellular extracts and confirmed that Δtpi#29 was lacking detectable levels of triose phosphate isomerase activity.

Δtpi#29 may be crossed to other yeast strains to form diploids that are heterozygous for the tpi$^-$ deletion. Such diploids may be sporulated so that other strains deficient for triose phosphate isomerase can be generated. For example, Δtpi#29 has been crossed to E8-10A (MATα leu2) (a spore segregant of the cross E2-7B[ATCC 20689]xGK100[ATCC 20669]) to form the diploid, E11. This diploid has been sporulated to generate the haploid descendant E11-3C, which has the following genotype: MATα pep4-3 tpi1. E11-3C has been crossed back to Δtpi#29 to form a diploid, E18, that is homozygous for the tpi1 deletion. E18 may be preferred over Δtpi#29 as a host strain for a plasmid because it has no amino acid requirements, has larger cells, and grows faster. These tpi$^-$ strains are deleted for the genetic material which codes for the glycolytic function and are, therefore, expected to be nonreverting (i.e., stable) mutants.

C. Transformation of the POT1 gene into *S. cerevisiae* tpi$^-$ deletion strains The plasmids pFPOT and pFATPOT were transformed into Δtpi#29 and related tpi$^-$ deletion strains. The yeast mutants were grown aerobically overnight to late log phase in YEP-2% Galactose at 30°. Transformation conditions were as described by Beggs (ibid.), except that the cells were allowed to recover at 30° for 1–2 hours in 1M Sorbitol containing YEP-3% Glycerol-1% Lactate or YEP-2% Galactose, instead of YEP-Dextrose, before plating the cells in top agar. The top agar and plates contained synthetic, modified Wickerham's medium with 1M Sorbitol and 2% Dextrose. After three days at 30°, transformants were visible and were picked out of the agar for replating onto YEPD. Thereafter, the transformants were maintained on YEPD or other complex media containing dextrose.

Strain E18 transformed with pFATPOT was designated ZYM-3. It has been deposited with ATCC under accession number 20699.

Stability of pFPOT and pFATPOT on complex media

To study plasmid stability, colonies from a single cell were inoculated into tubes containing YEPD and allowed to grow to a total population of $10^9$ cells (approximately 30 divisions). The yeast cells were sonicated to break up clumps, diluted to appropriate numbers, and plated onto YEP-2% Galactose or YEP-2% Glycerol-1% Lactate, which allows the growth of tpi$^-$ cells (with or without the plasmids carrying the POT1 gene). The colonies which arose on YEP-Galactose were then replica plated onto YEPD to screen for the loss of the plasmid (i.e., tpi$^-$ cells which have lost the POT1-containing plasmid will not grow on dextrose). The results, summarized in Table 2, indicate that the pFPOT and pFATPOT plasmids are stable in the yeast tpi$^-$ deletion strains. They are surprisingly much more stable than yeast plasmids containing centromeres. Centromere-bearing plasmids (which are low in copy number) are among the most stable plasmids reported for yeast and are generally lost at a frequency of around 1% of cells per division on complex media (see Murray and Szostak, ibid., for a review of centromere plasmid stability). As Table 2 indicates, the POT1 plasmids described herein are lost at a frequency of less than 1% after 30 divisions on complex media in tpi$^-$ deletion strains.

TABLE 2

STABILITY OF POT1 PLASMIDS VS. pTPICIO

| Experiment | Plasmid/Strain | Total Colonies[a] | TPI$^{+b}$ | % Loss[c] |
|---|---|---|---|---|
| 1 | pTPICIO/Δtpi#29 | 234 | 163 | 30.3 |
| 2 | pFPOT/Δtpi#29 | 308 | 308 | 0 |
| 3 | pFATPOT/Δtpi#29 | 471 | 471 | 0 |
| 4 | pFATPOT/E18(ZYM-3) | 1104 | 1104 | 0 |
| 5 | pFATPOT/E18(ZYM-3) | 634 | 632 | 0.32 |
| 6 | pFATPOT/Δtpi#29 | 426 | 426 | 0 |
| 2–6 | pooled data | 2943 | 2941 | 0.07 |

[a]The plasmid/strain combinations were grown on YEPD plates until easily visible colonies of approximately $10^4$ to $10^5$ cells were seen. These colonies were used to inoculate 6 ml of YEPD liquid medium. The cultures were grown aerobically overnight to a cell density of 1-3 × $10^8$ cells/ml and were plated onto YEP-2% Glycerol-1% Lactate or YEP-2% Galactose. Each of these media would allow tpi$^-$ strains to grow, although the resulting tpi– colonies arose more slowly than tpi$^+$ colonies. Only 100–300 cells were distributed on each plate so that each colony (whether tpi$^-$ or tpi$^+$ would be counted.
[b]The colonies were replica plated onto synthetic media containing dextrose at a 2% final concentration. Cells which had lost the triose phosphate isomerase gene on the plasmids were unable to grow.
[c]The "% Loss" represents the frequency of cells that had lost the plasmid after nearly 30 divisions in YEPD. The pooled data for experiments 2 to 6 indicate that the POT1 plasmids are extremely stable over these many divisions and are lost at a combined frequency well below 1% in 30 cell doublings.

D. Expression of human alpha-1-antitrypsin in *S. cerevisiae* using POT1 plasmids To test the use of the POT1 plasmids for enhancing expression of foreign proteins in a transformed yeast, plasmids pFATPOT and pFAT5 were used to transform *S. cerevisiae* strains Δtpi#29 and E2-7B respectively. Transformed cells were selected in leucineless media containing dextrose. Cultures were grown at 30° to an O.D.$_{600}$ of 3-4. Cell extracts were prepared and assayed for AT as described in Example 5.

AT produced by pFATPOT/Δtpi#29 represented 4–6% of total soluble protein. AT produced by pFAT5/E2-7B represented 2–3% of total soluble protein.

Although plasmid copy numbers are difficult to accurately measure and represent a population average, empirical observations of gene product quantities provide an indication of relative plasmid levels, given that the expression unit (promoter, gene of interest, terminator) remains the same. pFATPOT therefore appears Ito be functionally greater in number than pFAT5, from which it was derived. Because the two transformed strains are nearly identical genetically (Δtpi#29 being derived from E2-7B by plasmid-directed mutagenesis) and were grown under the same conditions, these results are indicative of the value of the herein-described stable plasmid expression system over previously described vectors.

E. Construction of pMPOT2 Vector

A second stable expression vector comprising the REP1, REP2, REP3 and ori sequences from yeast 2 micron DNA and the POT1 gene was constructed. The POT1 gene was obtained from pFATPOT by digestion of the plasmid with Sal I and Bam HI. This 1600 bp fragment was then ligated to pIC19R (comprising the polylinker sequence shown in FIG. 9 inserted into the Hind III site of pUC19 [Norrander et al., *Gene* 26:101–106, 1983]; see also Marsh et al., *Gene* 32:481–486, 1984), which had first been linearized by digestion with Sal I and Bam HI. The Bam HI, Pst I and Sal I sites in the resultant plasmid were destroyed in two steps to produce plasmid pICPOT*. The Pst I and Sal I sites were removed by cutting with Pst I and Sal I; the ends were blunted by digesting the Pst I 3' overhang with DNA polymerase I (Klenow fragment) and filling in the Sal I 5' overhang with Klenow fragment. The blunt ends were then ligated. The Bam HI site was then removed by cutting the plasmid with Bam HI, filling in the ends with DNA polymerase I (Klenow fragment) and religating the blunt ends.

The 2µ sequences were obtained from the plasmids YEp13 (Broach et al., *Gene* 8:121–133, 1979) and CI/1. The REP3 and ori sequences were removed from YEp13 by digestion with Pst I and Xba I and gel purification. REP2 was obtained from CI/1 by digestion with Xba I and Sph I and gel purification. The two fragments were then joined to pUC18 (Norrander et al., ibid.) which had been linearized with Pst I and Sph I to produce plasmid pUCREP2,3. REP1 was obtained from C1/1 by digestion with Eco RI and Xba I and gel purification of the 1704 bp fragment. The Eco RI-Xba I fragment was cloned into pUC13 which had been linearized with Eco RI and Xba I. The resultant plasmid was designated pUC13+REP1. The pUC13+REP1 plasmid was cut with Hind II and ligated in the presence of Eco RI linkers (obtained from Bethesda Research Laboratories). The REP1 gene was then removed as an Eco RI fragment of approximately 1720 bp. This Eco RI fragment was cloned into pIC7 (comprising the polylinker sequence shown in FIG. 9 inserted into the Hind III site of pUC8; Marsh et al., ibid.), which had been linearized with Eco RI. The resultant plasmid Was designated pICREPi#9.

To construct the final expression vector pMPOT2, pICPOT* was linearized by a partial Hind III digestion and complete Sst I digestion. Plasmid pUCREP2,3 was cut with Hind III and Sst I, and the fragment comprising REP2, REP3 and ori sequences was gel purified and joined to the linearized pICPOT*. The resultant plasmid, comprising REP2, REP3, ori POT1 and amp$^r$ sequences, was designated pMPOT1. REP1 was then removed from pICREP1#9 as a Bgl II-Nar I fragment and was ligated to pMPOT1, which had been cleaved with Bgl II and Nar I. The product of this ligation was designated pMPOT 2 (FIG. 10). *S. cerevisiae* strain Δtpi#29 transformed with pMPOT2 has been deposited with American Type Culture Collection under accession number 20744.

EXAMPLE 3

Preparation of Plasmid CI/1

CI/1 was constructed from plasmid, pJDB219 (Beggs, J., *Nature* 275, 104–109 (1978)). The pMB9 sequences were removed from pJDB248 by partial digestion with Eco RI and were replaced by pBR322 DNA which was cut with Eco RI. The restriction map of CI/1 is given in FIG. 6. The CI/1 plasmid contains the entire 2-micron DNA from yeast (*S. cerevisiae*), with a pBR322 insertion at an EcoRI site. It also contains the LEU2 gene.

EXAMPLE 4

Preparation of Plasmid pFAT5

The gene coding for the predominant form of human alpha-a-antitrypsin (AT) was isolated from a human liver cDNA library by conventional procedures using the baboon sequence (Kurachi et al., *Proc. Natl. Acad. Sci. USA* 78:6826–6830, 1980; and Chandra et al., *Biochem. Biophys. Res. Comm.* 103:751–758, 1981) as a DNA hybridization probe. The library was constructed by inserting human liver cDNA into the PstI site of the plasmid pBR322 (Bolivar et al., *Gene* 2:95–113, 1977). The AT gene was isolated from the library as a 1500 base pair (bp) PstI fragment. This fragment was inserted into the PstI site of pUC13 to produce the plasmid pUCα1. In pUCα1, the AT sequence is flanked on the 3' end by XbaI and EcoRI sites in the polylinker.

The TPI terminator was purified from plasmid pFG1 (Alber and Kawasaki, ibid.) as a XbaI-EcoRI fragment of approximately 700 bp and inserted into pUCα1 which had been cleaved with XbaI and EcoRI. This construct was then cut with EcoRI, and an EcoRI-BamHI oligonucleotide adapter (sequence:

AATTCATGGAG
GTACCTCCTAG)

were added, in multiple linked copies, to provide a BamHI site to the 3' end of the TPI terminator. The resultant plasmid is known as BAT5.

The TPI promoter fragment was obtained from plasmid pTPIC10 (Alber and Kawasaki, ibid.). This plasmid was cut at the unique KpnI site, the TPI coding region was removed with Bal31 exonuclease, and an EcoRI linker (sequence: GGAATTCC) was added to the 3' end of the promoter. Digestion with BglII and EcoRI yielded a TPI promoter fragment having BglII and EcoRI sticky ends. This fragment was then joined to plasmid YRp7' (Stinchcomb, et al. *Nature* 282:39–43, 1979) which had been cut with BglII and EcoRI. The resulting plasmid, TE32, was cleaved with EcoRI and BamHI to remove a portion of the tetracycline resistance gene. The linearized plasmid was then recircularized by the addition of the above described EcoRI-BamHI linker to produce plasmid TEA32. TEA32 was then cleaved with BGIII and BamHJI, and the TPI promoter was purified as a fragment of approximately 900 bp.

To construct plasmid pFAT5, plasmid CI/1 was linearized with BamHI, and was joined to the 900 bp TPI promoter fragment from TEA32. The resulting construct, known as plasmid F, has a unique BamHI site located at the 3' end of the TPI promoter. This plasmid was cut with BamHI and a 2200 bp BamHI fragment, comprising the AT coding sequence and TPI terminator, was purified from BAT5 and inserted into the BAMHI site. The resulting plasmid, known as pFAT5, is illustrated in FIG. 7.

EXAMPLE 5

Assay for Alpha-1-Antitrypsin

As a control, 10 microliters (1 microgram) of a solution of 100 microgram/ml trypsin, 100 microgram (100 microliters) of bovine serum albumin and 100 microliters of 0.05 molar TRIS, pH 8.0 buffer containing 1 mM benzoylargininoyl-p-nitroanilide were mixed, and the increase in absorbance at 405 nm was measured over time in a spectrophotometer. The absorbance value of this solution was used as a standard for 100% trypsin activity. All assayed samples contain equal concentrations of substrate and bovine serum albumin.

EXAMPLE 6

Expression of v-sis Sequences using POT1 Plasmids

The v-sis gene of simian sarcoma virus (SSV) encodes a protein designated p28$^{sis}$, which has been implicated as the transforming protein of the virus. The p28$^{sis}$ protein has been shown to be antigenically and structurally similar to platelet-derived growth factor (PDGF). The v-sis gene has been cloned and its DNA sequence determined (Devare et al., Proc. Natl. Acad. Sci. USA 79:3179, 1982; Devare, et al., Proc. Natl. Acad. Sci. USA 80:731, 1983). Portions of this gene were expressed in yeast using POT1 plasmids.

The SSV retroviral genome was cloned from SSV-11 nonproductively infected normal rat kidney cells which had SSV integrated into the genome (Devare et al., 1982, ibid.). The SSV DNA was isolated as 5.8 kb Eco RI fragment and subsequently inserted into pBR322 to produce plasmid pSSV-11. A 1.2 kb v-sis fragment was then purified from a Pst I digest of pSSV-11 and inserted into the Pst I site of pUC13. The resulting plasmid was designated pVSIS/Pst.

The v-sis sequences were then joined to a portion of the yeast mating pheromone alpha-factor (MFα1) gene (Kurjan and Herskowitz, Cell 30:933–943, 1982) to produce a secretory expression unit. Plasmid pSSV-11 was digested with Bam HI and Pvu II and the digestion products were electrophoresed through a 1.1% agarose gel extracted, and ethanol precipitated. The Hph I cleavage site was blunted using DNA polymerase I (Klenow fragment). The DNA was resuspended, digested with Hph I, and the 396 bp Hph I-Pvu II fragment was purified on a 1.25% agarose gel. The Hph I cleavage site was blunted using DNA polymerase I (Klenow fragment). The DNA was then digested with Bgl II and the 296 bp Hph I-Bgl II fragment (5' v-sis fragment) was gel purified. The 3' v-sis sequence was isolated from plasmid pVSIS/Pst as a 756 bp Bgl II-Xba I fragment. Plasmid p192, containing a 1700 bp Eco RI fragment comprising the MFα1 gene inserted into the Eco RI site of pUC13, was digested with Hind III, DNA polymerase I (Klenow fragment) and all four deoxyribonucleotides were then added to the reaction mixture. The DNA was then extracted with phenol/CHCl$_3$/ether, concentrated, and digested with Eco RI. The 1.2 kb Eco RI-Hind III (blunted) fragment comprising the promoter and secretory signal sequences of the MFα1 gene was then isolated by electrophoresis on a 0.9% agarose gel. Equimolar amounts of the 5' v-sis, 3' v-sis and MFα1 fragments plus Eco RI+Xba I digested pUC12 (Vieira and Messing, ibid., and Messing, ibid.) were then ligated together. The resultant plasmid was designated pVSα (FIG. 11).

A second MFα1/v-sis hybrid gene was constructed in which the first 66 codons of the v-sis sequence were deleted so that codon 67 of v-sis would immediately follow the codons for the Lys-Arg processing signal of pro alpha-factor. To precisely remove codons 1–66 of v-sis, oligonucleotide directed mutagenesis was performed essentially according to the two primer method of Zoller and Smith (Manual for Advanced Techniques in Molecular Cloning Course, Cold Spring Harbor Laboratory, 1983). A template was prepared by digesting pVSα with Xba I, purifying the 2.2 kb MFα1-v-sis fragment, ligating it to Xba I digested M13mp11 (replicative form) and isolating the positive strand DNA from transfected E. coli JM101. This clone was designated m11VSα.

One-half pmole of m11VSα was annealed with 1 pmole of kinased oligonucleotide ZC130 (3'AGA AAC CTA TTT TCC TCG GAC CCA$^5$') and 1.5 pmoles of universal sequencing primer (BRL) using conditions described (Zoller and Smith, ibid.), except that the annealing mixture was first heated to 65° C. for 10 minutes, shifted to 37° C. for 10 minutes, and then quickly chilled on ice. The annealed mixture was then treated with Klenow polymerase as described by Zoller and Smith (ibid.) to create circular duplex DNA. Portions of the elongation mixture were used to transform E. coli K12 JM101. The resulting phage plaques were screened for the proper deletion by transfer onto nitrocellulose filters and subsequent hybridization with $^{32}$p phosphorylated ZC130 at 65° C. Correctly juxtaposed sequences formed stable duplexes with the radioactive probe at the stringent hybridization temperature employed. Approximately 1% of the transformants screened gave positive signals by autoradiography. Ten clones were plaque-purified and replicative form DNA was prepared for restriction enzyme analysis. Five isolates showed the expected 1450 bp Hind III-Bgl II fragment. DNA sequence analysis of two isolates confirmed the correct fusion junction had been made, thus maintaining the proper translational reading frame. One of these phage was designated m11VS2α (FIG. 12).

For expression in yeast, the VSα and VS2α expression units (comprising the MFα1 and v-sis sequences) were then placed adjacent to the yeast TPI1 terminator in the following manner. The TPI1 terminator fragment was obtained form plasmid pFG1 (Alber and Kawasaki, ibid.). It encompasses the region from the penultimate amino acid codon of the TPI1 gene to the Eco RI site approximately 700 base pairs downstream. A Bam HI site was substituted for this unique Eco RI site of pFG1 by first cutting the plasmid with Eco RI, then blunting the ends with DNA polymerase I (Klenow fragment), adding synthetic Bam HI linkers (CGGATCCA), and re-ligating to produce plasmid p136. The TPI1 terminator was then excised from p136 as a Xba I-Bam HI fragment. This fragment was ligated into YEp13 which had been linearized with Xba I and Bam HI. The resulting plasmid is known as p213. The Hind III site was then removed from the TPI1 terminator region of p213 by digesting the plasmid with Hind III, blunting the resultant termini with DNA polymerase I (Klenow fragment), and recircularizing the linear molecule using T$_4$ DNA ligase. The resulting plasmid is p270.

Plasmid p270 was digested with Xba I and treated with calf alkaline phosphatase to prevent religation of the cohesive vector ends. v-sis expression units VSα and VS2α were prepared by Xba I digestion and agarose gel purification of pVSα and m11VS2α (replicative form), respectively. Each of the isolated fragments was ligated with an approximately equimolar amount of the phosphatased p270 vector in the presence of 40 units T$_4$ DNA ligase and the ligation mixtures transformed into E. coli RR1. Plasmid DNA was prepared from ampicillin-resistant colonies and restriction enzyme analysis performed in order to identify clones which possessed the TPI terminator adjacent to 3' v-sis sequences. Presence of 3.3 kb or 3.1 kb Bgl II fragments after gel electrophoresis indicted the correct orientation of YEpVSα and YEpVS2α, respectively (FIG. 13).

The VSα and VS2α sequences were then inserted into the stable vectors pCPOT and PMPOT2 and the yeast TPI1 promoter was substituted for the MFα1 promoter. The TPI1 promoter was obtained from plasmid pM220 (FIG. 14). E. coli RR1 transformed with pM220 has been deposited with American Type Culture Collection under accession number 39853.

Plasmid pM220 was digested with Bgl II and Bam HI, electrophoresed through a 0.9% agarose gel, and the 2.2 kb TPI1 promoter, MFα1 gene fragment extracted. The purified fragment was digested with Pst I and the resulting 1 kb Bgl II-Pst I fragment agarose gel-purified as above. Plasmid YEpVS2α was digested with Pst I and Bam Hi, and the 1.8 kb MFα1/v-sis/TPI1 terminator fusion fragment gel-isolated. Plasmid pCPOT was digested with Bam HI, treated with calf alkaline phosphatase, phenol/CHCl₃ extracted, then purified by electrophoresis through agarose, extracted from the gel and EtOH precipitated.

Approximately equimolar amounts of the three isolated fragments were ligated overnight at 12° C. and the ligation mixture used to transform *E. coli* K-12 strain DH1 (Hanahan, D. and Meseleson, M., *J. Mol. Biol.* 166:577, 1983) to ampicillin resistance. Plasmid DNA was prepared from transformants and restriction digest analysis used to verify the presence of the desired ~1500 bp Bam HI-Sal I fragment and 800 bp Sph I fragment. This plasmid was designated p117-2 (FIG. 14).

Plasmid YEpVS2α was digested with Pst I and Bam HI and the 1.8 kb fragment comprising the partial MFα1, v-sis, and TPI1 terminator sequences was purified by agarose gel electrophoresis. Plasmid pIC19R was digested with Pst I and Bam HI, and the vector fragment was gel purified and joined to the 1.8 kb fragment from YEpVS2α to produce plasmid pVS2αT.

Plasmid pM220 was digested with Bgl II and Pst I, and the ca. 1 kb fragment comprising the TPI1 promoter and the 5' portion of the MFα1 sequence was isolated and cloned in Bgl II+Pst I digested pIC19R. The resultant plasmid was digested with Cla I and Pst I, and the TPI1 promoter—MFα1 fragment was gel purified. Plasmid pVS2αT was then cut with Cla I and Pst I and joined to the TPI1 promoter-MFα1 fragment. The correct construct was identified by the presence of a 2.6 kb Cla I—Bam HI fragment wand was designated pTVS2αT (FIG. 14).

Approximately 10 μg of plasmid pVSα were digested with Bst EII to completion in a volume of 20 μl. Five units of Pst I were added, the mixture was incubated 30 minutes and the reaction stopped by the addition of EDTA. The quenched reaction mixture was immediately electrophoresed through a 1% agarose gel, and the ca. 800 bp partial Pst I-Bst EII band (comprising most of the MFα1 prepro sequence and the 5' portion of v-sis) was cut out, extracted from the gel, and EtOH precipitated.

Plasmid pTVS2αT was digested to completion with Pst I and Bst EII and purified by agarose gel electrophoresis. The resulting ca. 4.8 kb fragment and the 800 bp Pst I-Bst EII fragment from pVSα were ligated in the presence of T₄ DNA ligase for 6 hours at room temperature, and the ligation mixture was used to transform *E. coli* HB101 to ampicillin resistance. A plasmid was identified which contained a ca. 1450 bp Bgl II fragment, Which indicated the presence of the insert. It was designated pTVSα.

Plasmid ptVSα was digested to completion with Cla I and Bam HI, and the ca. 2.9 kb fragment containing the VSα sequences was isolated by electrophoresis through agarose, extraction from the gel, and EtOH precipitation. The ca. 2.9 kb Cla I-Bam HI VSα fragment was ligated with Cla I and Bam HI digested pMPOT2. The resultant vector was designated as pVSαm.

Plasmid pTVS2αT was digested to completion with Cla I and Bam HI in Bam HI buffer. The buffer was adjusted to high salt (Maniatis et al., ibid.) and the DNA was digested to completion with Pvu I, which cuts the vector sequences twice and permits resolution of the ca. 2.7 kb Cla I-Bam HI fragment containing the VS2α sequences on an agarose gel. This fragment was electrophoresed through 0.9% agarose, extracted, and EtOH precipitated. The fragment was then ligated with Cla I-Bam HI digested pMPOT2 in the presence of T₄ DNA ligase for 20 hours at 13° C. The ligated DNA was used to transform *E. coli* HB101 to ampicillin resistance, and plasmid DNA was prepared from the resulting colonies. A plasmid was identified which contained the 2.7 kb Cla I-Bam HI VS2α fragment was designated pVS2αm.

Plasmid pTVSαT was digested to completion with Cla I and Bam HI in Bam HI buffer. The buffer was adjusted to high salt (Maniatis et al., ibid.) and the DNA was digested to completion with Pvu I, which cuts the vector sequences twice and permits resolution of the ca. 2.7 kb Cla I-Bam HI fragment containing the Vs2α sequences on an agarose gel. This fragment was electrophoresed through 0.9% agarose, extracted, and EtOH precipitated. The fragment was then ligated with Cla I-Bam HI digested pMPOT2 in the presence of T₄ DNA ligase for 20 hours at 13° C. The ligated DNA was used to transform *E. coli* HB101 to ampicillin resistance, and plasmid DNA was prepared from the resulting colonies. A plasmid was identified which contained the 2.7 kb Cla I-Bam HI VS2α fragment was designated pVS2αm.

Expression vectors containing v-sis sequences were transformed into appropriate yeast host strains and the culture media assayed for the presence of PDGF-like material by enzyme linked immunosorbent assay (ELISA). YEp13-derived plasmids were transformed into *S. cerevisiae* E8c (MATα leu2 pep4). Plasmids p117-2, pVSαm, and pVS2αm were transformed into tpi⁻ deletion strains. Transformants were grown in appropriate media (–leu synthetic medium for YEp13 plasmids, YEPD for pMPOT2-derived plasmids) at 30° C. to stationary phase on a rotary shaker at 220 rpm. Cultures were harvested, the cells removed by centrifugation, and the media assayed as described below. Results are given in Table 3. Expression levels of v-sis sequences on POT1 plasmids are 5–8 times greater than on conventional yeast vectors.

TABLE 3

| EXPRESSION OF v-sis USING POT1 AND YEp13-DERIVED VECTORS | |
|---|---|
| Plasmid/Strain | PDGF (ng/ml) |
| YEpVSα/E8-11C | 0.5–1.5 |
| pVSαm/E18 | 4–10 |
| YEpVS2α/E8-11C | 0.8–2.0 |
| p117-2/E11-3C | 5–10 |
| pVS2αm/E18 | 6–14 |

Detection of PDGF-like Material by Enzyme-Linked Immunosorbent Assay (ELISA)

The expression of PDGF-like molecules by the yeast transformants was examined by ELISA and quantitated by comparison to a standard curve developed with purified human PDGF (Raines and Ross, *J. Biol. Chem.* 257:5154, 1982). A typical standard curve was prepared as follows. Purified human PDGF, 2.5 ng/ml in PBS, was incubated overnight with Immulon II (Dynatech Laboratories, Inc.) 96-well microtiter plates (100 μl/well) at 4° C. This coating solution was removed and 100 μl/well of 0.1% rabbit albumin in PBS was added and the plates incubated for 1 hour at 37° C. Samples of purified PDGF (0.1–40 ng/ml) were separately incubated with goat anti-PDGF IgG (5 μg/ml) in PBS containing 0.05% Tween 20 and 1 mg/ml rabbit albumin (RSA). The microtiter plates were washed 5 times with 0.9% NaCl, 0.05% Tween 20, drained and 100 μl of each test solution was added to the microtiter wells and incubated 2 hours at 37° C. The plates were washed as before, and peroxidase-conjugated swine anti-goat IgG (Tago, Inc.) diluted 1:1000 in PBS containing 0.05% tween 20 and 1 mg/ml RSA was added for 2 hours at 37° C. The plates were washed as before and freshly prepared 0.4% o-phenylene diamine containing 0.012% hydrogen peroxide (100 μl/well) was added for 50 minutes at room temperature and the reaction stopped at 50 minutes by the addition of 4N $H_2SO_4$ (50 μl/well). Absorbance at 492 nm was determined using a Dynatech plate scanner. Each test point was measured in triplicate.

Yeast culture media samples were diluted in PBS, assayed as described and compared to the PDGF standard curve. Table 3 is a summary of assay results for a representative series of experiments.

EXAMPLE 7

*Aspergillus nidulans* TPI cDNA as Selectable Marker

A functional TPI cDNA was isolated from *A. nidulans* by its ability to complement the TPI deletion in *S. cerevisiae* strain Δtpi29 (McKnight et al., *Cell* 46:143–147, 1986). The 1.15 kb TPI cDNA was inserted into pUC19 as an Eco RI-Bam HI fragment. The cDNA was excised from the resultant plasmid by partial digestion with Sst I and complete digestion with Bam HI. This fragment was inserted into Sst I-BglII digested pIC19R (Marsh, et al., *Gene* 32:481–486, 1984) to produce plasmid pM144. A Bam HI site was introduced into pM144 by linearizing the plasmid with Eco RV, adding a Bam HI linker sequence, and religating. The resultant construct was designated pM147. The TPI cDNA was then isolated from pM147 as a Sal I-Bam HI fragment.

Two stable plasmids containing the *A. nidulans* TPI selectable marker were constructed. Plasmid pCPOT (FIG. 6) was cut with Bam HI and Sph I to remove a 750 bp sequence from the 2μ portion of the plasmid pBR322 was digested with Bam HI and Sph I and a 186 bp fragment was purified and joined to the linearized pCPOT to construct pDPOT. The Sal I-Bam HI *A. nidulans* TPI fragment was then inserted into pDPOT and Cl/1 (Example 3), each of which had been linearized by digestion with the same enzymes. The pDPOT and Cl/1 derived vectors were designated pTIP and pCTIP, respectively. Plasmid pTIP was then tested for stability in a yeast transformant. *S. cerevisiae* strain GA18-1c (MATα leu2-3,112 ura3 bar1 Δtpi::LEU2) was transformed with pTIP and grown on glucose medium. The plasmid was shown to complement the TPI deletion in the host strain and to be present in high copy number (ca. 200 copies per cell), based on a comparison with ribosomal DNA bands on ethidium bromide stained gels. These results also indicate that a promoter sequence on the vector was fortuitously directing the expression of the TPI sequence. Further analysis showed that the *E. coli* lacz promoter on the pUC13 portion of pDPOT was responsible.

In order to test the effect of promoter strength on plasmid copy number and stability, the *A. nidulans* ADH3 and *S. cerevisiae* GAL1,10 promoters were inserted into pTIP 5' to the TPI cDNA. The ADH3 promoter was obtained from plasmid pM020 (McKnight et al., *EMBO J.* 4:2093–2099, 1985) as a Pst I-Hind III fragment of ca. 450 bp. This fragment was inserted into pIC19R (Marsh et al., ibid.) to yield plasmid pM051. The promoter was removed from pM051 by digestion with XhoI. A 685 bp Bam HI-Eco RI fragment comprising the GAL1,10 promoter (Johnston and Davis, *Mol. Cell. Biol.* 4:1440–1448, 1984) was inserted into pIC19H (Marsh et al., ibid.) to produce pRS80. Plasmid pRS80 was then digested with Sal I and Xho I and the GAL1,10 promoter was purified. The promoter fragments (ADH3 or GAL1,10) were then inserted into pTIP at the Sal I site 5' to the TPI cDNA and the resulting plasmids were designated pPROTIP and pGALTIP, respectively (FIG. 16A and 16B). The *A. nidulans* ADH3 promoter is weak due to its heterologous origin, which should result in inefficient transcription leading to increased copy number. The GAL1, 10 promoter is particularly advantageous since yeast transformants can be selected on galactose, where the promoter is induced, and the copy number therefore low. Subsequently, the transformants can be transferred to glucose as a carbon source so that the copy number can increase gradually as the GAL1,10 promoter is repressed. Both pPROTIP and pGALTIP were transformed into *S. cerevisiae* strain GA18-1C. pGALTIP transformants were selected on galactose and transferred to glucose media. Copy number of the plasmids was measured by comparison with ribosomal DNA bands on stained gels. Data indicate that pGALTIP is present at two to three times the copy number of pTIP. The use of strain GA18-1C is exemplary only. Any Δtpi strain (such as Δtpi#29; see Example 2B) may be used as host.

EXAMPLE 8

PGI Gene as Selectable Marker

A. Cloning of PGI

A yeast DNA library in the shuttle vector YEp13 was prepared as described by Nasmyth and Tatchell (*Cell* 19:753–764, 1980). A plasmid carrying the phosphoglucose isomerase (PGI) gene was identified by complementation of a pgi⁻ yeast strain, using simultaneous selection for growth on glucose and leucine prototrophy (Kawasaki and Fraenkel, *Biochem. Biophys. Res. Comm.* 108:1107–1112, 1982) and was designated pPGI19-7. Restriction endonuclease mapping of pPGI19-7 identified a 5.7 kb Bam HI-Hind III fragment which contained the PGI1 gene.

The PGI1-containing insert from pPGI19-7 was then subcloned into pUC13. The 5.3 kb fragment was obtained by cutting the plasmid to completion with Bam HI and partially with Hind III, followed by isolation on an agarose gel. The purified fragment was then ligated to pUC13 which had been cut with Bam HI and Hind III. The identity of the clone was confirmed by DNA sequencing. The resultant clone was designated pUCPGI.

B. Construction of PGI Deletion Strains

A plasmid was then constructed for use in disrupting the genomic PGI1 locus in yeast host strains. Most of the PGI coding sequence was removed from pUCPGI by digestion with BglII and SalI. The larger fragment (5.2 kb), comprising the PGI1 flanking sequences and pUC sequences was purified on a agarose gel. YEp13 was digested with BglII and SalI and the LEU2 fragment was similarly purified. The two fragments were ligated together and the DNA used to transform *E. coli* RR1 to ampicillin resistance. A plasmid having the desired insertion of LEU2 in the PGI1 gene was designated pGD1040 (FIG. 17).

Plasmid pGD1040 was then digested with Bam HI and Hind III and the fragment comprising the LEU2 sequence was used to transform *S. cerevisiae* strain E2-7B. Transformants were selected on −leu synthetic medium containing fructose. LEU⁺ transformants were then screened for the inability to grow on YEPD plates.

To confirm that the mutants were deficient in PGI, enzyme assays were carried out on crude cell extracts essentially as described by Maitra and Lobo (*J. Biol. Chem.* 246:475–488, 1971) and Kawasaki and Fraenkel, ibid. The cells were grown for 48 hours in 5 ml of YEPF medium (2% Bactopeptone, 1% yeast extract, 2% fructose) at 30° C. The cells were washed once with 5 ml of water and resuspended in 0.5 ml of 50 mM $K_2HPO_4$, 2 mM EDTA, 2 mM 2-mercaptoethanol, 1 mM PMSF, pH7.4. Extracts were prepared by disruption of the cells in a vortex mixer with an equal volume of 0.45 mm diameter glass beads. Cell debris was removed by centrifugation. The supernatants were then assayed for PGI activity by coupling the F6P to G6P reaction to the NADP to NADPH linked dehydrogenase reaction. The rate of NADPH production was measured by monitoring the absorbance at 340 nm. The deletion mutants showed no enzyme activity. One such mutant was designated #51 (MATa leu2 Δpgil::LEU2).

To obtain a pgi deletion strain that carries the trp1⁻ phenotype, strain #51 was crossed with *S. cerevisiae* strain G2 (MATα his3-Δ1 leu2-3,112 trp1-289 ura3-52). The diploid was sporulated and about 20 tetrads were dissected and screened for the inability to grow on either rich glucose medium or synthetic medium lacking tryptophan. One segregant was found to carry both the pgi deletion and the trp1⁻ phenotype. It was designated #51a (MATa leu2 trp1-289 ura3-52 his3-Δ1 Δpgil::LEU2).

C. Isolation of PGI cDNA

A yeast cDNA pool in plasmid pYcDE8 (McKnight et al., *EMBO J.* 4:2093–2099, 1985) was prepared essentially as described by McKnight and McConaughy (*Proc. Natl. Acad. Sci. USA* 80:4412–4416, 1983) and used to transform strain #51a. Transformants were selected on synthetic glucose medium lacking tryptophan. One transformant was obtained. Plasmid DNA was prepared from this transformant and was used to transform *E coli* RR1. Restriction mapping of the plasmid, designated pPGIcDNA, showed the PGI cDNA to be contained on a 2.0 kb Sst I-Bam HI fragment which corresponded to a portion of the 5.4 kb genomic fragment and overlapped considerably with the deleted portion of pGD1040 which had been used in the gene disruption. The cDNA was subcloned into M13 phage vectors and sequenced by conventional procedures. The sequence was in agreement with the amino acid composition of yeast phosphoglucose isomerase (Kempe et al., *J. Biol. Chem.* 249:4625–4633, 1974).

D. Use of PGI Plasmids as Expression Vectors

Plasmid pPGIcDNA was digested with Sst I and Bam HI and the 2.0 kb fragment comprising the PGI cDNA was gel purified. The cDNA was then ligated to pZUC13 which had been digested with SstI and Bam HI. (pZUC13 comprises the *S. cerevisiae* chromosomal LEU2 gene and the origin of replication from the *S. cerevisiae* 2 um plasmid inserted into pUC13. It was constructed in a manner analogous to pZUC12, described in published European patent application 195,691, using the plasmid pMT212, which is described in published European patent application 163,529.) The resulting plasmid, designated pA1 (FIG. 18), thus contains the PGI cDNA fused to the lacz promoter, the LEU2 sequence, the 2 micron origin of replication, and the ampicillin resistance marker. When pA1 was transformed into strain #51a, transformants grew on −leu glucose plates, indicating that the lacz promoter functioned in the yeast cells.

The plasmid copy number was then determined. Strain #51a transformed With pA1 was grown on complex medium (YEPD) and plasmid DNA was prepared. The DNA was cut with Sst I, run on an agarose gel and stained with ethidium bromide. By comparison with the ribosomal DNA bands, the copy number was estimated to be about 100 per cell.

E. Expression of Alpha-1-Antitrypsin Using PGI Selection

Plasmid pAl-B, comprising the expression unit of TPI promoter-alpha-1-antitrypsin coding sequence-TPI terminator inserted into pal was then constructed.

The expression unit was assembled in the following manner (FIG. 19). Plasmid TEA32 (Example 4) was digested with Bgl II and Eco RI and the 990 bp partial TPI promoter fragment was gel purified. Plasmid pIC19H was cut with Bgl II and Eco RI and the vector fragment was gel purified. The TPI promoter fragment was then ligated to the linearized pIC19H and the mixture was used to transform *E. coli* RR1. Plasmid DNA was prepared and screened for the presence of a 900 bp Bgl II-Eco RI fragment. A correct plasmid was selected and designated pICTPIP.

Plasmid pMVR1 was then assembled. Plasmid pIC7 (Marsh et al., ibid.) was digested with Eco RI, the fragment ends blunted with DNA polymerase I (Klenow fragment), and the linear DNA recircularized using T4 DNA ligase. The resulting plasmid was used to transform *E. coli* RR1. Plasmid DNA was prepared from the transformants and screened for the loss of the Eco RI site. A plasmid having the correct restriction pattern was designated pIC7RI*. Plasmid pIC7RI, was digested with Hind III and Nar I and the 2500 bp fragment was gel purified. The partial TPI promoter fragment (ca. 900 bp) was removed from pICTPIP using Nar I and Sph I and was gel purified. pFATPOT was digested with Sph I and Hind III and the 1750 bp fragment comprising the partial TPI promoter, the AT cDNA, and the TPI terminator was gel purified. The pIC7RI* fragment, the partial TPI promoter fragment, and the partial TPI promoter-AT-TPI terminator fragment from pFATPOT were then combined in a triple ligation to produce pMVR1.

The expression vector for alpha-1-antitrypsin was then constructed. Plasmid pMVR1 was digested with Bgl II and the 2.3 kb expression unit fragment (TPI1 promoter —AT cDNA—TPI1 terminator) was gel purified and inserted into the Bam HI site of pal. The resulting plasmid was designated pA1-B (FIG. 19).

pA1-B was transformed into *S. cerevisiae* strain #51a and the transformants were grown on YEPD liquid medium to an O.D. 600 of 11. The transformants expressed alpha-1-antitrypsin at 2.5%–4.0% of total soluble protein, comparable to the levels obtained using POT1 selection. The copy number of pA1-B was approximately 100 per cell.

F. Expression of Tissue Type Plasminogen Activator (tPa)

Plasmid pDR1396 prepared as described in copending commonly assigned U.S. patent application Ser. No. 663, 068 filed Oct. 18, 1984 comprises the expression unit of TPI1 promoter-alpha factor prepro-tPA cDNA-TPI1 terminator in pUC18. The tPA cDNA sequence is described by Pennica et al. (*Nature* 301:214–221, 1983). The alpha factor gene (MFα1) is described by Kurjan and Herskowitz (*Cell* 30:933–943, 1982). In pDR1396 the MFα1 prepro sequence is joined to the tPA cDNA to produce a primary translation product having the sequence (MFα1 prepro)-Lys-Arg-Glu-Ala-Glu-Ala-Gly-Arg-Ser-(tPA) at the junction. The expression unit was removed from pDR1396 by digesting the plasmid completely with Bam HI and partially with Bgl II. The 3.5 kb fragment was then purified on an agarose gel. This fragment was inserted into the Bam HI site of pal to produce plasmids pA1-1398a and pA1-1398b. The plasmids were used to transform strain #51a and tPA expression levels were assayed by ELISA and fibrinolysis assay. The transformants produced between 10 and 20 ug of tPA per liter of culture.

The fibrin lysis assay is based on the method of Binder et al. (*J. Biol. Chem.* 254: 1998, 1979). 10 ml of a bovine fibrinogen solution (3.0 mg/ml in 0.036M sodium acetate pH 8.4, 0.036M sodium barbital, 0.145M NaCl, $10^{-4}$M $CaCl_2$, 0.02% $NAN_3$) were added to 10 ml of a 1.5% solution of low melting temperature agarose in the same buffer at 40° C. To this solution were added 10 μl of bovine thrombin (500 U/ml). The mixture was poured onto a Gelbond agarose support sheet (Marine Colloids) and allowed to cool. Wells were cut in the agarose and to the wells were added 10 μl of the sample to be tested plus 10 μl of phosphate buffered saline containing 0.1% bovine serum albumin. Relsults were compared to a standard curve prepared using purified tPA. The development of a clear halo around the well indicates the presence of biologically active plasminogen activator.

What is claimed is:

1. A method for producing a protein product in a yeast host cell having a deficiency in a function necessary for normal cell growth on complex media comprising the steps of:
   (a) transforming a yeast host cell having a deficiency in a cell cycle or glycolytic enzyme gene with a DNA molecule comprising a gene which complements said deficiency and a sequence coding for said protein product; and
   (b) culturing the cell from step (a) under normal growth conditions in a growth medium whereby said gene functions as a selectable marker for cells transformed with said DNA molecule in the absence of additional selective pressure.

2. A method according to claim 1 wherein said gene is a yeast CDC4 gene.

3. A method according to claim 1 wherein said gene is a triose phosphate isomerase gene.

4. A method according to claim 3 wherein said gene is a *Schizosaccharomyces pombe* triose phosphate isomerase gene.

5. A method according to claim 3 wherein said gene is an *Aspergillus nidulans* triose phosphate isomerase gene.

6. A method according to claim 1 wherein said gene is a yeast phosphoglucose isomerase gene.

7. A method according to claim 1 wherein said gene is from a cell species different from said hose cell.

8. A method for selecting transformed yeast cells comprising the steps of:
   (a) subjected yeast cells having a deficiency in a cell cycle or glycolytic enzyme gene to transforming conditions in the presence of a DNA construct comprising a gene which complements said deficiency; and
   (b) subjecting the cells from step (a) to normal growth conditions in a nutrient medium whereby said gene functions as a selectable marker for cells transformed with said DNA molecule in the absence of additional selective pressure and whereby transformed cells remain viable and multiply while untransformed cells fail to multiply due to said deficiency.

9. A method according to claim 8 wherein said gene is a yeast CDC4 gene.

10. A method according to claim 8 wherein said gene is a yeast phosphoglucose isomerase gene.

11. A method according to claim 8 wherein said gene is operably linked to a repressible promoter.

12. A method according to claim 8 wherein said gene is a triose phosphate isomerase gene.

13. A method according to claim 1 wherein said yeast host cell is a *Saccharomyces cerevisiae* cell.

14. A method according to claim 13 wherein said gene is a *Schizosaccharomyces pombe* triose phosphate isomerase gene.

15. A method according to claim 13 wherein said gene is an *Aspergillus nidulans* triose phosphate isomerase gene.

16. A method according to claim 1 wherein said yeast host cell is a *Saccharomyces cerevisiae* cell and said gene is a *Saccharomyces cerevisiae* gene selected from the group consisting of genes encoding the enzymes pyruvate kinase, triose phosphate isomerase, phosphoglucose isomerase, phosphoglycerate mutase, phosphoglycerate kinase, phospho-fructokinase, kexokinase and glucokinase, and the regulatory gene, GCR1.

17. A method according to claim 1 wherein said gene is operably linked to a repressible promoter.

18. A method according to claim 1 wherein said gene is selected from the group consisting of genes encoding the enzymes pyruvate kinase, triose phosphate isomerase, phosphoglucose isomerase, phosphoglycerate mutase, phosphoglycerate kinase, phospho-frucEokinase, kexokinase and glucokinase, and the regulatory gene, GCR1.

19. A method according to claim 1 wherein said yeast host cell is a *Saccharomyces cerevisiae* cell.

20. A method according to claim 1 wherein said gene is selected from the group consisting of genes encoding the enzymes pyruvate kinase, triose phosphate isomerase, phosphoglucose isomerase, phosphoglycerate mutase, phosphoglycerate kinase, phospho-fructokinase, kexokinase and glucokinase; and the regulatory gene, GCR1.

* * * * *